US010286065B2

(12) United States Patent
Dickey et al.

(10) Patent No.: US 10,286,065 B2
(45) Date of Patent: May 14, 2019

(54) COMPOSITIONS AND METHODS FOR TREATING VIRAL INFECTIONS THROUGH STIMULATED INNATE IMMUNITY IN COMBINATION WITH ANTIVIRAL COMPOUNDS

(71) Applicants: Board of Regents, The University of Texas System, Austin, TX (US); Pulmotect, Inc., Houston, TX (US); Baylor College of Medicine, Houston, TX (US)

(72) Inventors: Burton Dickey, Houston, TX (US); Scott Evans, Bellaire, TX (US); Brian Gilbert, Houston, TX (US); Diane Markesich, Houston, TX (US); Brenton Scott, Houston, TX (US); Michael Tuvim, Houston, TX (US)

(73) Assignees: BOARD OF REGENTS, THE UNIVERSITY OF TEXAS SYSTEM, Austin, TX (US); BAYLOR COLLEGE OF MEDICINE, Houston, TX (US); PULMOTECT, INC., Houston, TX (US)

( * ) Notice: Subject to any disclaimer, the term of this patent is extended or adjusted under 35 U.S.C. 154(b) by 0 days.

(21) Appl. No.: 14/860,205

(22) Filed: Sep. 21, 2015

(65) Prior Publication Data

US 2016/0082103 A1 Mar. 24, 2016

Related U.S. Application Data

(60) Provisional application No. 62/053,013, filed on Sep. 19, 2014, provisional application No. 62/053,610, filed on Sep. 22, 2014.

(51) Int. Cl.

| | | |
|---|---|---|
| *A61K 39/39* | (2006.01) | |
| *A61K 38/08* | (2019.01) | |
| *A61K 31/24* | (2006.01) | |
| *A61K 9/00* | (2006.01) | |
| *A61K 45/06* | (2006.01) | |
| *A61K 31/215* | (2006.01) | |
| *A61K 31/7056* | (2006.01) | |
| *A61K 38/05* | (2006.01) | |
| *A61K 38/06* | (2006.01) | |
| *A61K 38/07* | (2006.01) | |
| *A61K 39/00* | (2006.01) | |

(52) U.S. Cl.
CPC ............ *A61K 39/39* (2013.01); *A61K 9/0078* (2013.01); *A61K 31/215* (2013.01); *A61K 31/24* (2013.01); *A61K 31/7056* (2013.01); *A61K 38/05* (2013.01); *A61K 38/06* (2013.01); *A61K 38/07* (2013.01); *A61K 38/08* (2013.01); *A61K 45/06* (2013.01); *A61K 2039/55561* (2013.01); *Y02A 50/388* (2018.01)

(58) Field of Classification Search
None
See application file for complete search history.

(56) References Cited

U.S. PATENT DOCUMENTS

| | | | |
|---|---|---|---|
| 3,608,066 A | 9/1971 | Illartein | 424/46 |
| 4,406,889 A | 9/1983 | Hartmann et al. | 514/2.3 |
| 4,406,890 A | 9/1983 | Tarcsay et al. | 514/20.9 |
| 4,423,038 A | 12/1983 | Baschang et al. | 514/2.3 |
| 4,439,425 A | 3/1984 | Tarcsay et al. | 424/177 |
| 4,666,886 A | 5/1987 | Baschang et al. | 514/17 |
| 4,668,218 A | 5/1987 | Virtanen | 604/58 |
| 4,689,338 A | 8/1987 | Gerster | 514/293 |
| 4,929,624 A | 5/1990 | Gerster et al. | 514/293 |
| 5,238,944 A | 8/1993 | Wick et al. | 514/293 |
| 5,266,575 A | 11/1993 | Gerster et al. | 514/293 |
| 5,268,376 A | 12/1993 | Gester | 514/293 |
| 5,346,905 A | 9/1994 | Gerster | 514/293 |
| 5,352,784 A | 10/1994 | Nikolaides et al. | 544/126 |
| 5,389,640 A | 2/1995 | Gerster et al. | 514/293 |
| 5,395,937 A | 3/1995 | Nikolaides et al. | 546/82 |
| 5,432,157 A | 7/1995 | Metzger et al. | 514/2.4 |
| 5,458,135 A | 10/1995 | Patton et al. | 128/200.14 |
| 5,494,916 A | 2/1996 | Lindstrom et al. | 514/303 |
| 5,525,612 A | 6/1996 | Gerster | 514/293 |
| 5,700,910 A | 12/1997 | Metzger et al. | 530/338 |
| 6,024,964 A | 2/2000 | Jung et al. | 424/208.1 |
| 6,039,969 A | 3/2000 | Tomai et al. | 424/434 |
| 6,066,447 A | 5/2000 | De Mesmaeker et al. | 435/5 |
| 6,110,929 A | 8/2000 | Gerster et al. | 514/293 |
| 6,214,806 B1 | 4/2001 | Krieg et al. | 514/44 |
| 6,218,371 B1 | 4/2001 | Krieg et al. | 514/44 R |
| 6,239,116 B1 | 5/2001 | Krieg et al. | 514/44 A |
| 6,288,042 B1 | 9/2001 | Rando et al. | 514/44 A |

(Continued)

FOREIGN PATENT DOCUMENTS

| | | |
|---|---|---|
| EP | 1 550 458 | 7/2005 |
| EP | 1 707 232 | 8/2010 |

(Continued)

OTHER PUBLICATIONS

Da Dalt et al. Oseltamivir-resistant pandemic (H1N1) 2009 treated with nebulized zanamivir. Emerg Infect Dis. Nov. 2010;16(11):1813-5.*
Gilbert et al. MegaRibavirin aerosol for the treatment of influenza A virus infections in mice. Antiviral Res. Jun. 2008;78(3):223-9. Epub Feb. 4, 2008. (Year: 2008).*
"TLR 2/6/9 agonist PUL-042", NCI Drug Dictionary, available online, May 4, 2018.*
Abuchowski et al., "Effect of covalent attachment of polyethylene glycol on immunogenicity and circulating life of bovine liver catalase," J. Biol. Chem., 252:3582-6, 1977.
Adachi et al., "Targeted disruption of the MyD88 gene results in loss of IL-1- and IL-18-mediated function ," Immunity, 9:143-150, 1998.

(Continued)

*Primary Examiner* — Nianxiang Zou
(74) *Attorney, Agent, or Firm* — Norton Rose Fulbright US LLP

(57) ABSTRACT

Embodiments are directed to compositions and methods for treating viral infections.

11 Claims, 4 Drawing Sheets

Specification includes a Sequence Listing.

(56) References Cited

U.S. PATENT DOCUMENTS

| | | | |
|---|---|---|---|
| 6,294,177 B1 | 9/2001 | Fattom | 424/243.1 |
| 6,331,539 B1 | 12/2001 | Crooks et al. | 514/228.5 |
| 6,339,068 B1 | 1/2002 | Krieg et al. | 514/44 R |
| 6,406,705 B1 | 6/2002 | Davis et al. | 424/278.1 |
| 6,429,199 B1 | 8/2002 | Krieg et al. | 514/44 |
| 6,451,810 B1 | 9/2002 | Coleman et al. | 514/293 |
| 6,488,953 B2 | 12/2002 | Halliday et al. | 424/434 |
| 6,517,839 B1 | 2/2003 | Modlin et al. | 424/190.1 |
| 6,534,062 B2 | 3/2003 | Raz et al. | 424/193.1 |
| 6,552,006 B2 | 4/2003 | Raz et al. | 514/44 R |
| 6,727,230 B1 | 4/2004 | Hutcherson et al. | 514/44 R |
| 6,737,045 B2 | 5/2004 | Patton et al. | 424/46 |
| 6,794,357 B1 | 9/2004 | Backstrom et al. | 514/7.4 |
| 6,797,258 B2 | 9/2004 | Platz et al. | 424/45 |
| 6,815,429 B2 | 11/2004 | Agrawal et al. | 514/44 R |
| 6,929,798 B2 | 8/2005 | Pillich et al. | 424/243.1 |
| 6,949,520 B1 | 9/2005 | Hartmann et al. | 514/44 R |
| 6,977,245 B2 | 12/2005 | Klinman et al. | 514/44 R |
| 7,001,890 B1 | 2/2006 | Wagner et al. | 514/44 R |
| 7,038,029 B2 | 5/2006 | Lopez et al. | 536/23.1 |
| 7,105,495 B2 | 9/2006 | Agrawal et al. | 514/44 R |
| 7,115,579 B2 | 10/2006 | Agrawal et al. | 514/44 A |
| 7,157,437 B2 | 1/2007 | Nest | 514/44 |
| 7,176,296 B2 | 2/2007 | Agrawal et al. | 536/23.1 |
| 7,271,156 B2 | 9/2007 | Krieg et al. | 514/44 A |
| 7,276,489 B2 | 10/2007 | Agrawal et al. | 514/44 R |
| 7,276,515 B2 | 10/2007 | Dellaria et al. | 514/293 |
| 7,329,409 B2 | 2/2008 | Pillich et al. | 424/243.1 |
| 7,358,068 B2 | 4/2008 | Vaillant et al. | 435/91.1 |
| 7,371,734 B2 | 5/2008 | Phillips et al. | 514/44 R |
| 7,381,807 B2 | 6/2008 | Lopez et al. | 536/22.1 |
| 7,393,859 B2 | 7/2008 | Coleman et al. | 514/293 |
| 7,402,572 B2 | 7/2008 | Krieg et al. | 514/44 R |
| 7,405,204 B2 | 7/2008 | Roberts et al. | 514/42 |
| 7,405,285 B2 | 7/2008 | Agrawal et al. | 536/23.1 |
| 7,408,050 B2 | 8/2008 | Kim et al. | 536/23.1 |
| 7,410,975 B2 | 8/2008 | Lipford et al. | 514/266.2 |
| 7,425,548 B2 | 9/2008 | Nair et al. | 514/60 |
| 7,427,405 B2 | 9/2008 | Agrawal et al. | 424/277.1 |
| 7,427,629 B2 | 9/2008 | Kedl et al. | 514/279 |
| 7,488,490 B2 | 2/2009 | Davis et al. | 424/278.1 |
| 7,491,706 B2 | 2/2009 | Yu et al. | 514/44 R |
| 7,498,425 B2 | 3/2009 | Agrawal et al. | 536/23.1 |
| 7,498,426 B2 | 3/2009 | Agrawal et al. | 536/23.1 |
| 7,507,802 B2 | 3/2009 | Ahn et al. | 536/23.1 |
| 7,517,861 B2 | 4/2009 | Krieg et al. | 514/44 R |
| 7,521,063 B2 | 4/2009 | Klinman et al. | 424/282.1 |
| 7,534,772 B2 | 5/2009 | Weiner et al. | 514/44 R |
| 7,544,697 B2 | 6/2009 | Hays et al. | 514/293 |
| 7,550,501 B2 | 6/2009 | Chow et al. | 514/419 |
| 7,566,702 B2 | 7/2009 | Agrawal et al. | 514/44 R |
| 7,566,703 B2 | 7/2009 | Krieg et al. | 514/44 R |
| 7,569,553 B2 | 8/2009 | Krieg et al. | 514/44 R |
| 7,576,066 B2 | 8/2009 | Krieg et al. | 514/44 R |
| 7,585,847 B2 | 9/2009 | Bratzler et al. | 514/44 R |
| 7,598,382 B2 | 10/2009 | Hays et al. | 546/82 |
| 7,605,138 B2 | 10/2009 | Krieg et al. | 514/44 R |
| 7,612,083 B2 | 11/2009 | Griesgraber et al. | 514/292 |
| 7,615,539 B2 | 11/2009 | Uhlmann et al. | 514/44 R |
| 7,713,529 B2 | 5/2010 | Krieg et al. | 424/184.1 |
| 7,723,022 B2 | 5/2010 | Krieg et al. | 435/5 |
| 7,884,083 B2 | 2/2011 | Van Nest et al. | 514/44 |
| 8,158,592 B2 | 4/2012 | Krieg et al. | 514/44 |
| 8,158,768 B2 | 4/2012 | Dina et al. | 536/23.1 |
| 8,226,957 B2 | 7/2012 | Van Nest | 424/211.1 |
| 8,283,328 B2 | 10/2012 | Krieg et al. | 514/44 |
| 8,309,527 B2 | 11/2012 | Krieg et al. | 514/44 |
| 8,518,905 B2 | 8/2013 | Hackam | 514/44 |
| 8,871,732 B2 | 10/2014 | Dina et al. | 514/44 |
| 8,883,174 B2 | 11/2014 | Dickey et al. | 424/278.1 |
| 9,186,400 B2 | 11/2015 | Dickey et al. | |
| 2002/0045737 A1 | 4/2002 | Choi et al. | 536/23.1 |
| 2002/0142977 A1 | 10/2002 | Raz et al. | 514/44 R |
| 2003/0091599 A1 | 5/2003 | Davis et al. | 424/278.1 |
| 2003/0148976 A1 | 8/2003 | Krieg et al. | 514/44 R |
| 2003/0181406 A1 | 9/2003 | Schetter et al. | 514/44 R |
| 2003/0212028 A1 | 11/2003 | Raz et al. | 514/44 R |
| 2003/0224010 A1 | 12/2003 | Davis et al. | 424/185.1 |
| 2003/0225016 A1 | 12/2003 | Fearon et al. | 514/44 R |
| 2003/0232074 A1 | 12/2003 | Lipford et al. | 424/450 |
| 2004/0006032 A1 | 1/2004 | Lopez et al. | 514/44 R |
| 2004/0009949 A1 | 1/2004 | Krieg et al. | 514/44 A |
| 2004/0053880 A1 | 3/2004 | Krieg et al. | 514/44 R |
| 2004/0058883 A1 | 3/2004 | Phillips et al. | 514/44 R |
| 2004/0067905 A1 | 4/2004 | Krieg et al. | 514/44 A |
| 2004/0087534 A1 | 5/2004 | Krieg et al. | 514/44 A |
| 2004/0091491 A1 | 5/2004 | Kedl et al. | 424/178.1 |
| 2004/0092472 A1 | 5/2004 | Krieg et al. | 514/44 R |
| 2004/0106568 A1 | 6/2004 | Krieg et al. | 514/44 R |
| 2004/0141950 A1 | 7/2004 | Noelle et al. | 424/85.1 |
| 2004/0152649 A1 | 8/2004 | Krieg et al. | 514/44 R |
| 2004/0152657 A1 | 8/2004 | Krieg et al. | 514/44 R |
| 2004/0162309 A1 | 8/2004 | Gorden et al. | 514/292 |
| 2004/0171086 A1 | 9/2004 | Fink et al. | 435/7.2 |
| 2004/0171150 A1 | 9/2004 | Krieg et al. | 435/375 |
| 2004/0171571 A1 | 9/2004 | Krieg et al. | 514/44 A |
| 2004/0181045 A1 | 9/2004 | Krieg et al. | 536/23.1 |
| 2004/0198680 A1 | 10/2004 | Krieg et al. | 514/44 R |
| 2004/0198688 A1 | 10/2004 | Krieg et al. | 514/44 R |
| 2004/0229835 A1 | 11/2004 | Krieg et al. | 514/44 R |
| 2004/0234512 A1 | 11/2004 | Wagner et al. | 424/93.21 |
| 2004/0235770 A1 | 11/2004 | Davis et al. | 514/44 R |
| 2004/0235777 A1 | 11/2004 | Wagner et al. | 514/44 R |
| 2004/0235778 A1 | 11/2004 | Wagner et al. | 514/44 R |
| 2004/0248834 A1 | 12/2004 | Klinman et al. | 514/44 R |
| 2004/0248837 A1 | 12/2004 | Raz et al. | 514/44 R |
| 2005/0004061 A1 | 1/2005 | Krieg et al. | 514/44 R |
| 2005/0004062 A1 | 1/2005 | Krieg et al. | 514/44 R |
| 2005/0009774 A1 | 1/2005 | Krieg et al. | 514/44 A |
| 2005/0013812 A1 | 1/2005 | Dow et al. | 424/144.1 |
| 2005/0026861 A1 | 2/2005 | Kandimalla et al. | 514/44 A |
| 2005/0032736 A1 | 2/2005 | Davis et al. | 514/44 A |
| 2005/0037403 A1 | 2/2005 | Krieg et al. | 435/6.14 |
| 2005/0043529 A1 | 2/2005 | Krieg et al. | 536/23.72 |
| 2005/0049215 A1 | 3/2005 | Krieg et al. | 514/44 A |
| 2005/0049216 A1 | 3/2005 | Krieg et al. | 514/44 A |
| 2005/0054601 A1 | 3/2005 | Wagner et al. | 514/44 A |
| 2005/0054602 A1 | 3/2005 | Krieg et al. | 514/44 A |
| 2005/0059619 A1 | 3/2005 | Krieg et al. | 514/44 A |
| 2005/0059625 A1 | 3/2005 | Krieg et al. | 514/44 R |
| 2005/0075302 A1 | 4/2005 | Hutcherson et al. | 514/44 R |
| 2005/0100983 A1 | 5/2005 | Bauer et al. | 435/68.1 |
| 2005/0101554 A1 | 5/2005 | Krieg et al. | 514/44 R |
| 2005/0107297 A1 | 5/2005 | Holmes et al. | 514/7.7 |
| 2005/0119273 A1 | 6/2005 | Lipford et al. | 514/252.17 |
| 2005/0123523 A1 | 6/2005 | Krieg et al. | 424/93.21 |
| 2005/0130911 A1 | 6/2005 | Uhlmann et al. | 514/26 |
| 2005/0130918 A1 | 6/2005 | Agrawal et al. | 514/44 A |
| 2005/0163764 A1 | 7/2005 | Medzhitov et al. | 424/93.45 |
| 2005/0169888 A1 | 8/2005 | Hartmann et al. | 424/85.7 |
| 2005/0171047 A1 | 8/2005 | Krieg et al. | 514/44 R |
| 2005/0175630 A1 | 8/2005 | Raz et al. | 424/203.1 |
| 2005/0181422 A1 | 8/2005 | Bauer et al. | 435/6.16 |
| 2005/0214359 A1 | 9/2005 | Stegmann | 424/450 |
| 2005/0215500 A1 | 9/2005 | Krieg et al. | 514/44 R |
| 2005/0215501 A1 | 9/2005 | Lipford et al. | 514/44 R |
| 2005/0222072 A1 | 10/2005 | Wang et al. | 514/44 R |
| 2005/0233995 A1 | 10/2005 | Krieg et al. | 514/44 R |
| 2005/0239733 A1 | 10/2005 | Jurk et al. | 514/44 A |
| 2005/0239734 A1 | 10/2005 | Uhlmann et al. | 514/44 A |
| 2005/0239735 A1 | 10/2005 | Miller et al. | 514/44 R |
| 2005/0239736 A1 | 10/2005 | Krieg et al. | 514/44 A |
| 2005/0244379 A1 | 11/2005 | Krieg et al. | 424/93.2 |
| 2005/0244380 A1 | 11/2005 | Krieg et al. | 424/93.2 |
| 2005/0244505 A1 | 11/2005 | Higbee et al. | 424/489 |
| 2005/0245477 A1 | 11/2005 | Krieg et al. | 514/44 A |
| 2005/0256073 A1 | 11/2005 | Lipford et al. | 514/44 R |
| 2005/0261215 A1 | 11/2005 | Garren et al. | 514/44 R |
| 2005/0276789 A1 | 12/2005 | Lopez et al. | 424/93.2 |
| 2005/0277604 A1 | 12/2005 | Krieg et al. | 514/44 R |
| 2005/0277609 A1 | 12/2005 | Krieg et al. | 514/44 A |
| 2005/0287612 A1 | 12/2005 | Benin et al. | 435/7.32 |
| 2006/0003955 A1 | 1/2006 | Krieg et al. | 514/44 R |
| 2006/0003962 A1 | 1/2006 | Ahluwalia et al. | 514/44 A |

(56) References Cited

U.S. PATENT DOCUMENTS

| | | |
|---|---|---|
| 2006/0009501 A1 | 1/2006 | Nair et al. .................. 514/367 |
| 2006/0014713 A1 | 1/2006 | Agrawal et al. ............ 514/44 A |
| 2006/0019916 A1 | 1/2006 | Krieg et al. ................ 514/44 A |
| 2006/0019919 A1 | 1/2006 | Agrawal et al. ............ 514/44 A |
| 2006/0019923 A1 | 1/2006 | Davis et al. ................ 514/44 A |
| 2006/0025365 A1 | 2/2006 | Agrawal et al. ............ 514/44 A |
| 2006/0058251 A1 | 3/2006 | Krieg et al. ................ 514/44 R |
| 2006/0089326 A1 | 4/2006 | Krieg et al. ................ 514/44 A |
| 2006/0094680 A1 | 5/2006 | Agrawal et al. ............ 514/44 A |
| 2006/0094681 A1 | 5/2006 | Agrawal et al. ............ 514/44 A |
| 2006/0094683 A1 | 5/2006 | Krieg et al. ................ 514/44 A |
| 2006/0140875 A1 | 6/2006 | Krieg et al. .................. 424/46 |
| 2006/0154890 A1 | 7/2006 | Bratzler et al. ............ 514/44 A |
| 2006/0172966 A1 | 8/2006 | Lipford et al. ............ 514/44 R |
| 2006/0188475 A1 | 8/2006 | Xu et al. .................... 424/85.2 |
| 2006/0188913 A1 | 8/2006 | Krieg et al. ................ 435/6.16 |
| 2006/0211644 A1 | 9/2006 | Krieg et al. ................ 514/44 A |
| 2006/0217328 A1 | 9/2006 | Kandimalla et al. ....... 514/44 A |
| 2006/0229271 A1 | 10/2006 | Krieg et al. ................ 514/44 R |
| 2006/0241076 A1 | 10/2006 | Uhlmann et al. ........... 514/44 R |
| 2006/0246035 A1 | 11/2006 | Ahluwalia et al. .......... 424/85.7 |
| 2006/0286070 A1 | 12/2006 | Hartmann et al. ........... 424/85.7 |
| 2006/0287263 A1 | 12/2006 | Davis et al. ................ 514/44 A |
| 2006/0292179 A1 | 12/2006 | Ducatelle et al. ......... 424/234.1 |
| 2007/0004654 A1 | 1/2007 | Raz et al. .................... 514/43 |
| 2007/0009482 A9 | 1/2007 | Krieg et al. .................. 424/93.2 |
| 2007/0010470 A9 | 1/2007 | Krieg et al. ................ 514/44 R |
| 2007/0026018 A1 | 2/2007 | Ellis et al. .................. 424/234.1 |
| 2007/0037767 A1 | 2/2007 | Bratzler et al. ............ 514/44 A |
| 2007/0049550 A1 | 3/2007 | Fearon et al. .............. 514/44 R |
| 2007/0066553 A1 | 3/2007 | Krieg et al. ................ 514/44 R |
| 2007/0066554 A1 | 3/2007 | Krieg et al. ................ 514/44 R |
| 2007/0078104 A1 | 4/2007 | Krieg et al. ................ 514/44 A |
| 2007/0129320 A9 | 6/2007 | Davis et al. ................ 514/44 R |
| 2007/0142315 A1 | 6/2007 | Forsbach et al. ........... 514/44 A |
| 2007/0167409 A1 | 7/2007 | Chow et al. .................... 514/80 |
| 2007/0179103 A1 | 8/2007 | Agrawal et al. ............ 514/44 A |
| 2007/0184465 A1 | 8/2007 | Wagner et al. .............. 435/6.16 |
| 2007/0202128 A1 | 8/2007 | Krieg et al. ................ 424/234.1 |
| 2007/0219153 A1 | 9/2007 | Kandimalla et al. ....... 514/44 R |
| 2007/0224210 A1 | 9/2007 | Krieg et al. ................ 424/185.1 |
| 2007/0232622 A1 | 10/2007 | Lipford et al. ............ 514/258.1 |
| 2008/0009455 A9 | 1/2008 | Krieg et al. ................ 514/44 R |
| 2008/0031936 A1 | 2/2008 | Krieg et al. .................. 424/450 |
| 2008/0045473 A1 | 2/2008 | Uhlmann et al. ........... 514/44 R |
| 2008/0070907 A1 | 3/2008 | Griesgraber et al. ...... 514/230.2 |
| 2008/0089883 A1 | 4/2008 | Kandimalla et al. ....... 424/130.1 |
| 2008/0113929 A1 | 5/2008 | Lipford et al. ............ 514/44 A |
| 2008/0114019 A1 | 5/2008 | Kshirsagar et al. .......... 514/293 |
| 2008/0124366 A1 | 5/2008 | Ohlfest et al. .............. 424/278.1 |
| 2008/0170996 A1 | 7/2008 | Dickey et al. ................ 424/45 |
| 2008/0171712 A1 | 7/2008 | Kandimalla et al. ....... 514/44 A |
| 2008/0193437 A1 | 8/2008 | Agrawal et al. ................ 514/1.1 |
| 2008/0193468 A1 | 8/2008 | Levy et al. ................ 424/184.1 |
| 2008/0207674 A1 | 8/2008 | Stoesz et al. ................ 514/293 |
| 2008/0226649 A1 | 9/2008 | Schetter et al. ............ 424/141.1 |
| 2008/0241139 A1 | 10/2008 | Delucia et al. .............. 424/135.1 |
| 2008/0249056 A1 | 10/2008 | Klinman et al. ............ 514/44 R |
| 2008/0269192 A1 | 10/2008 | Griesgraber et al. ...... 514/211.09 |
| 2008/0279785 A1 | 11/2008 | Kandimalla et al. ........ 514/1.1 |
| 2008/0292648 A1 | 11/2008 | Kandimalla et al. ....... 424/184.1 |
| 2008/0306252 A1 | 12/2008 | Crooks et al. ................ 534/798 |
| 2008/0312434 A1 | 12/2008 | Lindstrom et al. ........... 544/126 |
| 2008/0318998 A1 | 12/2008 | Prince et al. ................ 514/293 |
| 2009/0017021 A1 | 1/2009 | Davis et al. ................ 424/133.1 |
| 2009/0017075 A1 | 1/2009 | Van Nest et al. ........... 424/275.1 |
| 2009/0017076 A1 | 1/2009 | Miller et al. ................ 424/277.1 |
| 2009/0029988 A1 | 1/2009 | Kshirsagar et al. ....... 514/234.2 |
| 2009/0030031 A1 | 1/2009 | Kshirsagar et al. .......... 514/293 |
| 2009/0042925 A1 | 2/2009 | Kshirsagar et al. .......... 514/293 |
| 2009/0053148 A1 | 2/2009 | Kandimalla et al. ........... 424/45 |
| 2009/0053206 A1 | 2/2009 | Kandimalla et al. ...... 424/130.1 |
| 2009/0060898 A1 | 3/2009 | Kandimalla et al. ...... 424/130.1 |
| 2009/0060927 A1 | 3/2009 | Wagner et al. ............ 424/184.1 |
| 2009/0060937 A1 | 3/2009 | Lopez et al. .............. 424/193.1 |
| 2009/0062328 A1 | 3/2009 | Kshirsagar et al. .......... 514/293 |
| 2009/0069299 A1 | 3/2009 | Merrill et al. ............ 514/217.07 |
| 2009/0069314 A1 | 3/2009 | Kshirsagar et al. ....... 514/232.8 |
| 2009/0075980 A1 | 3/2009 | Hays et al. .............. 514/217.07 |
| 2009/0087388 A1 | 4/2009 | Kandimalla et al. .......... 514/1.1 |
| 2009/0087446 A1 | 4/2009 | Vollmer et al. ............. 424/185.1 |
| 2009/0098063 A1 | 4/2009 | Kandimalla et al. ........... 424/45 |
| 2009/0099122 A1 | 4/2009 | Klinman et al. ............. 514/44 R |
| 2009/0105295 A1 | 4/2009 | Kshirsagar et al. .......... 514/293 |
| 2009/0117132 A1 | 5/2009 | Readett et al. ............. 424/172.1 |
| 2009/0123460 A1 | 5/2009 | Noelle et al. ............... 424/130.1 |
| 2009/0124611 A1 | 5/2009 | Hays et al. ................. 514/232.8 |
| 2009/0137519 A1 | 5/2009 | Krieg et al. ................ 514/44 R |
| 2009/0142362 A1 | 6/2009 | Krieg et al. ................ 424/185.1 |
| 2009/0155307 A1 | 6/2009 | Davis et al. ................ 424/204.1 |
| 2009/0163532 A1 | 6/2009 | Perman et al. ................ 514/293 |
| 2009/0163533 A1 | 6/2009 | Hays et al. .................... 514/293 |
| 2009/0169529 A1 | 7/2009 | Hartmann et al. .......... 424/93.21 |
| 2009/0176696 A1 | 7/2009 | Mills et al. .................... 514/1.1 |
| 2009/0176821 A1 | 7/2009 | Kshirsagar et al. .......... 514/293 |
| 2009/0191188 A1 | 7/2009 | Krieg et al. ............... 424/130.1 |
| 2009/0208468 A1 | 8/2009 | Klinman et al. ............. 424/93.7 |
| 2009/0214578 A1 | 8/2009 | Bauer et al. ................ 424/184.1 |
| 2009/0220528 A1 | 9/2009 | Turka et al. ............... 424/173.1 |
| 2009/0253695 A1 | 10/2009 | Kshirsagar et al. ....... 514/232.8 |
| 2009/0263405 A1 | 10/2009 | Verthelyi et al. .......... 424/184.1 |
| 2009/0306017 A1 | 12/2009 | Kuritz ........................... 514/106 |
| 2009/0306177 A1 | 12/2009 | Uhlmann et al. ........... 514/44 A |
| 2009/0311277 A1 | 12/2009 | Krieg et al. ................ 424/184.1 |
| 2009/0318337 A1 | 12/2009 | Lowell et al. .................. 514/1.1 |
| 2009/0324639 A1 | 12/2009 | Lowell et al. ............. 424/206.1 |

FOREIGN PATENT DOCUMENTS

| | | |
|---|---|---|
| WO | WO 1994/06498 | 3/1994 |
| WO | WO 1994/08552 | 4/1994 |
| WO | WO 1994/16970 | 8/1994 |
| WO | WO 1997/25086 | 7/1997 |
| WO | WO 1998/16427 | 4/1998 |
| WO | WO 1998/35888 | 8/1998 |
| WO | WO 1998/55152 | 12/1998 |
| WO | WO 1998/55495 | 12/1998 |
| WO | WO 2002/046189 | 6/2002 |
| WO | WO 2002/046192 | 6/2002 |
| WO | WO 2003/035695 | 5/2003 |
| WO | WO 2003/067991 | 8/2003 |
| WO | WO 2008/085549 | 7/2008 |
| WO | WO 2010/111485 | 9/2010 |

OTHER PUBLICATIONS

Agrawal & Kandimalla, "Synthetic agonists of Toll-like receptors 7, 8 and 9", Biochemical Society Transactions, 2007, vol. 35, No. 6, pp. 1461-1467.

Akinbi et al., "Bacterial killing is enhanced by expression of lysozyme in the lungs of transgenic mice," J. Immunol., 165(10):5760-6, 2000.

Akira et al., "Role of adapters in Toll-like receptor signaling," Biochem. Soc. Trans., 31(Pt 3):637-42, 2003.

Aliprantis et al., "Cell activation and apoptosis by bacterial lipoproteins through toll-like receptor-2," Science, 285:736-739, 1999.

Apidianakis et al., "Profiling early infection responses: Pseudomonas aeruginosa eludes host defenses by suppressing antimicrobial peptide gene expression," Proc. Natl. Acad. Sci. U.S.A., 102:2573-2578, 2005.

Bafika et al., "Cutting edge: TLR9 and TLR2 signaling together account for MyD88-dependent control of parasitemia in Trypanosoma cruzi infection," J Immunol,. 177:3515-3519, 2006.

Bals and Hiemstra, "Antimicrobial peptides in COPD—basic biology and therapeutic applications ," Curr. Drug Targets, 7(6):743-50, 2006.

Bals and Hiemstra, "Innate immunity in the lung: how epithelial cells fight against respiratory pathogens ," Eur. Respir. J., 23(2):327-333. 20, 2004.

Bals et al., "Augmentation of innate host defense by expression of a cathelicidin antimicrobial peptide," Infect. Immun., 67:6084-6089, 1999.

(56) References Cited

OTHER PUBLICATIONS

Bals et al., "Mouse beta-defensin 3 is an inducible antimicrobial peptide expressed in the epithelia of multiple organs," Infect. Immun., 67:3542-3547, 1999.
Beauchamp et al., "A new procedure for the synthesis of polyethylene glycol-protein adducts; effects on function, receptor recognition, and clearance of superoxide dismutase, lactoferrin, and alpha 2-macroglobulin," Anal. Biochem., 131:25-33, 1983.
Becker et al., "CD14-dependent lipopolysaccharide-induced beta-defensin-2 expression in human tracheobronchial epithelium," J .Biol. Chem., 275:29731-29736, 2000.
Beckmann et al. Eur. J. Immunol. 2005, 35:282-289.
Bergmann and Schwarting, "Application of a polyvalent bacterial lusat as aerosol in patients with recurrent airway infections without detectable side effects," Allergologie, Jabrgang, 10:455-458, 1987 (German with English abstract).
Bernard, "Acute respiratory distress syndrome: a historical perspective," Am. J. Respir. Crit Care Med., 172:798-806, 2005.
Beutler, "TLRs and innate immunity ," Blood, 113:1399-1407, 2009.
Brown et al., "Complexities of targeting innate immunity to treat infection," Trends in Immunology, 28:260-6, 2007.
Buwitt-Beckmann et al., "Lipopeptide structure determines TLR2 dependent cell activation level ," FEBS J., 272:6354-6364, 2005.
Chen et al., "Properties of two urate oxidases modified by the covalent attachment of poly(ethylene glycol)," Biochim. Biophy. Acta, 660:293-298, 1981.
Clement et al., "Allergic lung inflammation alters neither susceptibility to *Streptococcus pneumoniae* infection nor inducibility of innate resistance in mice," Respir. Res., 10:70, 2009.
Clement et al., "Stimulation of innate immune defense protects against *S. pneumoniae* infection," Proc. Am. Thorac. Soc., 2, A452 (abstract), 2005.
Clement et al., "Stimulation of lung innate immunity protects against lethal pneumococcal pneumonia in mice ," Am. J. Respir. Crit. Care Med., 177:1322-1330, 2008.
Cluff et al., "Synthetic toll-like receptor 4 agonists stimulate innate resistance to infectious challenge," Infect. Immun., 73:3044-3052, 2005.
Cole et al., "Cationic polypeptides are required for antibacterial activity of human airway fluid," J .Immunol., 169:6985-6991, 2002.
Cole et al., "Decreased clearance of Pseudomonas aeruginosa from airways of mice deficient in lysozyme M," J. Leukoc. Biol., 78:1081-1085, 2005.
Dearman et al., "Toll-like receptor ligand activation of murine bone marrow-derived dendritic cells," Immunology, 126:475-484, 2009.
Deng et al., "CpG oligodeoxynucleotides stimulate protective innate immunity against pulmonary Klebsiella infection," J. Immunol., 173:5148-5155, 2004.
Dennis et al., "Tularemia as a biological weapon: medical and public health management," JAMA, 285:2763-2773, 2001.
Diamond et al., "Inducible expression of an antibiotic peptide gene in lipopolysaccharide-challenged tracheal epithelial cells," Proc. Natl. Acad. Sci. U.S.A., 93:5156-5160, 1996.
Diamond et al., "The innate immune response of the respiratory epithelium," Immunol. Rev., 173:27-38, 2000.
Drake et al., "Toll-Like Receptor-2/6 and Toll0Like Receptor-9 Agonists Suppress Viral Replication but Not Airway Hyperreactvity in Guinea Pigs" Am J Respir Cell Mol Biol, 48(6): 790-96, 2013.
Duggan et al. The Journal Immunology, 2011, 186:5916-5626.
Edwards et al., "Phosphatidylinositol 3-kinase/Akt signaling in the response of vascular endothelium to ionizing radiation," Cancer Res., 62:4671-4677, 2002.
Evans et al., "Inducible innate resistance of lung epithelium to infection ," Annu. Rev. Physiol., (72)413-35, 2010.
Evans et al., "Mucin is produced by clara cells in the proximal airways of antigen-challenged mice," Am. J. Respir. Cell Mol. Biol., 31(4):382-94, 2004.

Evans et al., "Pneumocystis cell wall beta-glucans stimulate alveolar epithelial cell chemokine generation through nuclear factor-kappaB-dependent mechanisms," Am. J. Respir. Cell Mol. Biol., 32(6): 490-497, 2005.
Evans et al., "Stimulated innate resistance of lung epithelium protects mice broadly against bacteria and fungi ," Am. J. Respir. Cell Molec. Biol., 42:40-50, 2010.
Fiegel et al., "Airborne infectious disease and the suppression of pulmonary bioaerosols," Drug Discov. Today, 11:51-57, 2006.
File, "Community-acquired pneumonia," Lancet, 362:1991-2001, 2003.
Finlay & McFadden, "Anti-immunology: evasion of the host immune system by bacterial and viral pathogens," Cell, 124:767-782, 2006.
Fischer & Voynow, "Neutrophil elastase induces MUC5AC gene expression in airway epithelium via a pathway involving reactive oxygen species," Am. J. Respir. Cell Mol. Biol., 26:447-452, 2002.
Forteza et al., "Regulated hydrogen peroxide production by Duox in human airway epithelial cells," Am. J. Respir. Cell Mol. Biol., 32(5):462-9, 2005.
Foxwell et al., "Mucosal immunization against respiratory bacterial pathogens," Expert. Rev. Vaccines, 2:551-60, 2003.
Ghosh et al., "Toll-like receptor (TLR) 2-9 agonists-induced cytokines and chemokines: I. Comparison with T cell receptor-induced responses," Cell Immunol, 243:48-57, 2006.
Gorden et al., "Synthetic TLR agonists reveal functional differences between human TLR7 and TLR8 ," J. Immunol., 174:1259-1268, 2005.
Hackett, "Innate immune activation as a broad-spectrum biodefense strategy: prospects and research challenges," J. Allergy Clin. Immunol., 112:686-694, 2003.
Hajjar et al., "An essential role for non-bone marrow-derived cells in control of Pseudomonas aeruginosa pneumonia," Am. J. Respir. Cell Mol. Biol., 33:470-475, 2005.
Hartmann et al., "Delineation of a CpG Phosphorothioate Oligodeoxynucleotide for Activating Primate Immune Responses In Vitro and In Vivo", The Journal of Immunology, 2000, vol. 164, pp. 1617-1624.
Hartmann et al., "Rational design of new CpG oligonucleotides that combine B cell activation with high IFN-alpha induction in plasmacytoid dendritic cells", Eur. J. Immunol. 2003, vol. 33, pp. 1633-1641.
Hashimoto et al., "The Toll gene of *Drosophila*, required for dorsal-ventral embryonic polarity, appears to encode a transmembrane protein," Cell, 52(2):269-279, 1988.
Hayashi et al., "The innate immune response to bacterial flagellin is mediated by Toll-like receptor 5," Nature, 410:1099-1103, 2001.
Hertz et al., "Activation of Toll-like receptor 2 on human tracheobronchial epithelial cells induces the antimicrobial peptide human beta defensin-2," J. Immuno., 171:6820-6826, 2003.
Hilleman, "Overview: cause and prevention in biowarfare and bioterrorism," Vaccine, 20:3055-3067, 2002.
Hoffman et al., "TLR-targeted therapeutics," Nature Reviews, 4:879-80, 2005.
Holtzman et al., "Immunity, inflammation, and remodeling in the airway epithelial barrier: epithelial-viral-allergic paradigm," Physiol. Rev., 82:19-46, 2002.
Homer et al., "Differential expression of chitinases identify subsets of murine airway epithelial cells in allergic inflammation," Am. J. Physiol Lung subsets of murine airway Cell Mol. Physiol., 291:L502-L511, 2006.
International Search Report and Written Opinion Issued in PCT/US2015/051233, dated Dec. 14, 2015.
International Search Report and Written Opinion issued in PCT/US2010/028658, dated Jul. 14, 2010.
International Search Report and Written Opinion, issued in Application No. PCT/US2009/056525, dated Mar. 26, 2010.
Ishii et al., "Host innate immune receptors and beyond: making sense of microbial infections," Cell Host and Microbe, 3:352-363, 2008.
Iwasaki, "Mucosal dendritic cells," Annu. Rev. Immunol., 25:381-418, 2007.
Janeway, Jr. & Medzhitov, "Innate immune recognition ," Annu Rev. Immunol., 20:197-216, 2002.

(56) References Cited

OTHER PUBLICATIONS

Jean et al., "Protective effect of endotoxin instillation on subsequent bacteria-induced acute lung injury in rats," Am. J. Respir. Crit. Care Med., 158:1702-1708, 1998.

Joos & Tamm, "Breakdown of pulmonary host defense in the immunocompromised host: cancer chemotherapy," Proc.Am.Thorac. Soc., 2:445-448, 2005.

Jurk et al., "C-Class CpG ODN: sequence requirements and characterization of immunostimulatory activities on mRNA level", Immunobiology, 2004, vol. 209, pp. 141-154.

Kaisho et al., "Toll-like receptors as adjuvant receptors," Biochim. Biophys. Acta, 1589(1):1-13, 2002.

Kearney et al., "Visualization of peptide-specific T cell induction in and peripheral tolerance induction in vivo ," Immunity, 1:327, 1994.

Kellner et al. Biol Chem Hoppe Seyler. Jan. 1992;373(1):51-5.

Kimbrell, et al., "Comparison of the Immunostimulatory and Proinflammatory Activities of Candidate Gram-Positive Endotoxins, Lipoteichoic Acid, Peptidoglycan, and Lipopeptides in Murine and Human Cells", Immunol. Lett., 2008; 118(2): 132-141.

Kingma & Whitsett, "In defense of the lung: surfactant protein A and surfactant protein D," Curr. Opin. Pharmacol., 6:277-283, 2006.

Kita et al., "Characterization of a polyethylene glycol conjugate of recombinant human interferon-gamma," Drug Des. Delivery, 6:157-167, 1990.

Klempt et al., "Identification of epithelial and myeloid-specific DNA elements regulating MRP14 gene transcription," J. Cell Biochem., 73:49-55, 1999.

Knauf et al., "Relationship of effective molecular size to systemic clearance in rats of recombinant interleukin-2 chemically modified with water-soluble polymers," J. Biol. Chem., 263:15064-15070, 1988.

Knowles & Boucher, "Mucus clearance as a primary innate defense mechanism for mammalian airways," J. Clin. Invest., 109:571-577, 2002.

Krieg et al., "CpG motifs in bacterial DNA trigger direct B-cell activation", Letters to Nature, vol. 374, pp. 546-549, Apr. 6, 1995.

Krieg, "Antiinfective Applications of Toll-like Receptor 9 Agonists", Proceedings of the American Thoracic Society, vol. 4, pp. 289-297, 2007.

Krieg, "Therapeutic potential of Toll-like receptor 9 activation", Nature Reviews, vol. 5, pp. 471-484, Jun. 2006.

Krishnan et al., "Toll-Like Receptor Signal Transduction," Experimental and Molecular Medicine, Aug. 2007, vol. 39, No. 4, pp. 421-438.

Krug et al., "Identification of CpG oligonucleotide sequences with high induction of IFN-alpha/beta in plasmacytoid dendritic cells," Eur. J. Immunol., 31:2154-2163, 2001.

Lee et al., "Differential modulation of Toll-like receptors by fatty acids: preferential inhibition by n-3 polyunsaturated fatty acids," J. Lipid Res., 44:479-486, 2003.

Lee et al., "Molecular basis for the immunostimulatory activity of guanine nucleoside analogs: activation of Toll-like receptor 7," Proc. Natl. Acad. Sci. USA, 100:6646-6651, 2003.

Lee et al., "TLR-4 pathway mediates inflammatory response but not bacterial elimination in E. coli pneumonia," Am. J. Physiol. Lung Cell Mol. Physiol., 289:L731-L738, 2005.

Legarda et al., "Suppression of NF-kappaB-mediated beta-defensin gene expression in the by the Bordetella type III secretion system," Cell Microbiol., 7:489-497, 2005.

Lemaitre et al., "The dorsoventral regulatory gene cassette spätzle/Toll/cactus controls the potent antifungal response in Drosophila adults," Cell, 86(6): 973-983, 1996.

Lin et al., "The murine L-plastin gene promoter: identification and comparison with the human L-plastin gene promoter," DNA Cell Biol., 16(1): 9-16, 1997.

Liu et al., "Toll-like receptor triggering of a vitamin D-mediated human antimicrobial response," Science, 311:1770-1773, 2006.

Martin & Frevert, 2005. "Innate immunity in the lungs," Proc. Am. Thorac. Soc., 2:403-411, 2005.

Martin et al., "Role of innate immune factors in the adjuvant activity of monophosphoryl lipid A," Infect. Immun., 71:2498-2507, 2003.

McHutchison et al., "Phase 1B, Randomized, Double-Blind, Dose-Escalation Trial of CPG 10101 in Patients with Chronic Hepatitis C Virus", Hepatology 2007, vol. 46, No. 5, pp. 1341-1349.

Medzhitov & Janeway, "Innate immunity: impact on the adaptive immune response," Curr. Opin. Immunol., 9:4-9, 1997.

Medzhitov & Janeway, Jr., "The Toll receptor family and microbial recognition," Trends Microbiol., 8(10):452-456, 2000.

Medzhitov et al., "MyD88 is an adaptor protein in the hToll/IL-1 receptor family signaling pathways," Mol. Cell, 2(2):253-258, 1998.

Merkus et al. Rhinology, 44, 102-107, 2006.

Moghaddam et al., "Haemophilus influenzae lysate induces aspects of the chronic obstructive pulmonary disease phenotype," Am. J. Respir. Cell Mol. Biol., 38:629-638, 2008.

Moghaddam et al., "Repetitive exposure to an aerosolized lysate of non-typeable Haemophilus influenzae recapitulates some aspects of the COPD phenotype," Am. J. Respir. Cell Mol. Biol., 2007.

Mondino et al., "The anatomy of T-cell activation and tolerance," Proc. Natl. Acad. Sci. USA, 93(6):2245-2252, 1996.

Moser et al., "beta-Defensin 1 contributes to pulmonary innate immunity in mice," Infect. Immun., 70:3068-3072, 2002.

Murphy et al., "Chapter 2: Innate Immunity," in Janeway C. Immunobiology, Seventh Edition, New York and London, Garland Science, pp. 39-103, Nov. 2007.

Nagase et al., "Expression and function of Toll-like receptors in eosinophils: activation by Toll-like receptor 7 ligand," J Immunol., 171(8):3977-3982, 2003.

Office Action issued in Chinese Patent Application No. 201080022634.7, dated Aug. 20, 2012.

Palma-Carlos & Palma Carlos, "Non specific immunomodulation in respiratory infections," Allergic et Immunologic, 22:179-185, 1990.

Pastva et al., "Immunomodulatory roles of surfactant proteins A and D: implications in lung disease," Proc. Am. Thorac. Soc., 4:252-257, 2007.

Platz et al., "Microbial DNA Induces a Host Defense Reaction of Human Respiratory Epithelial Cells", The Journal of Immunology, 2004, vol. 173, pp. 1219-1223.

Poltorak et al., "Defective LPS signaling in C3H/HeJ and C57BL/10ScCr mice: mutations in Tlr4 gene," Science, 282(5396):2085-2088, 1998.

Pulendran & Ahmed, "Translating innate immunity into immunological memory: implications for vaccine development," Cell, 124:849-863, 2006.

Pulendran et al., "Prevention of peripheral tolerance by a dendritic cell growth factor: flt3 ligand as an adjuvant," J. Exp. Med., 188(11):2075-2082, 1998.

Rogan et al., "Antimicrobial proteins and polypeptides in pulmonary innate defense," Respir. Res., 7:29, 2006.

Roman et al., "Immunostimulatory DNA sequences function as T helper-1-promoting adjuvants," Nat. Med., 3(8):849-854, 1997.

Sadikot et al. "Targeted immunomodulation of the NF-kappaB pathway in airway epithelium impacts host defense against Pseudomonas aeruginosa," J. Immunol., 176:4923-4930, 2006.

Sato et al., "Dual recognition of herpes simplex viruses by TLR2 and TLR9 in dendritic cells," Proc. Natl. Acad. Sci., 103:17343-17348, 2006.

Scott et al., "Stimulation of lung innate immunity protects against a broad range of infectious microbes," Mol. Biol. Cell., 18 (supp):A1336 (abstract), 2007.

Singh et al., "Production of beta-defensins by human airway epithelia," Proc. Natl. Acad. Sci. U.S.A., 95:14961-14966, 1998.

Song et al., "TLR4 initiated and cAMP mediated abrogation of bacterial invasion of the bladder," Cell Host. Microbe., 1:287-298, 2007.

Takeda & Akira, "Microbial recognition by Toll-like receptors," J. Dermatol. Sci., 34(2):73-82, 2004.

Takeda & Akira, "TLR signaling pathways," Semin. Immunol., 16:3-9, 2004.

Travis et al., "Antimicrobial peptides and proteins in the innate defense of the airway surface," Curr. Opin. Immunol., 13:89-95, 2001.

(56) References Cited

OTHER PUBLICATIONS

Trinchieri & Sher, "Cooperation of Toll-like receptor signals in innate immune defense," Nat. Rev. Immunol., 7:179-190, 2007.
Tsutsumi et al., "Polyethylene glycol modification of interleukin-6 enhances its thrombopoietic activity," J. Controlled Rel., 33:447-451, 1995.
Tuvim et al., "Augmented lung inflammation protects against influenza A pneumonia," PLoS One, 4:e4176, 2009.
Tuvim et al., "Synergistic TLR2/6 and TLR9 Activation Protects Mice against Lethal Influenza Pneumonia" PLoS One, 7: 1-9, 2012.
Ulevitch, "Therapeutics targeting the innate immune system," Nature Reviews, 4:512-20, 2004.
Vollmer & Krieg, "Immunotherapeutic applications of CpG oligodeoxynucleotide TLR9 agonists" Advanced Drug Delivery Reviews, 2009, vol. 61, pp. 195-204.
Vollmer et al., "Characterization of three CpG oligodeoxynucleotide classes with distinct immunostimulatory activities", Eur. J. Immunol., 2004, vol. 34, pp. 251-262.
Vroegop et al., "Pharmacokinetic properties, induction of interferon, and efficacy of selected 5-halo-6-phenyl pyrimidinones, bropirimine analogues, in a model of severe experimental autoimmune encephalomyelitis," Intl. J. Immunopharmacol., 21:647-662, 1999.
Wang et al., "Airway epithelia regulate receptor expression of human beta-defensin 2 through Toll-like receptor 2," FASEB J., 17:1727-1729, 2003.
Wang et al., "Novel cytoplasmic proteins of nontypeable Haemophilus influenzae up-regulate human MUC5AC mucin transcription via a positive p38 mitogen-activated protein kinase pathway and a negative phosphoinositide 3-kinase-Akt pathway," J. Biol. Chem., 277:949-957, 2002.
Weiser & Pan, "Adaption of Haemophilus influenzae to acquired and innate humoral immunity based on phase variation of lipopolysaccharide," Mol. Microbiol., 30:767-775, 1998.
Williams et al., "Airway mucus: From production to secretion," Am. J. Respir. Cell Mol. Biol., 34(5):527-36. 10, 2006.
Xingkui, et al. "Immunostimulatory characteristics and applications of CpG oligodeoxynucleotides" Progress in Veterinary Medicine, 2008, 29(7): 71-75. (English Abstract).
Yamamoto et al., "Role of adaptor TRIF in the MyD88-independent toll-like receptor signaling pathway," Science, 301:640-643, 2003.
Young et al., "A3 adenosine receptor signaling contributes to airway mucin secretion after allergen challenge," Am. J. Respir. Cell Mol. Biol., 35:549-558, 2006.
Young et al., "Central Role of Muc5ac Expression in Mucous Metaplasia and Its Regulation by Conserved 5' Elements," Am. J. Respir. Cell Mol. Biol., 37:273-290, 2007.
Zhen et al., "IL-13 and epidermal growth factor receptor have critical but distinct roles in epithelial cell mucin production," Am. J. Respir. Cell Mol. Biol., 36:244-253, 2007.

\* cited by examiner

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
tcgtcgtttt cggcgcgcgc cg                                              22

```
<210> SEQ ID NO 2
<211> LENGTH: 25
<212> TYPE: DNA
<213> ORGANISM: Artificial Sequence
<220> FEATURE:
<223> OTHER INFORMATION: Synthetic Primer

<400> SEQUENCE: 2
tcgtcgtcgt tcgaacgacg ttgat                                  25

<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
tcgtcgtttt cgcgcgcgcc g                                      21

<210> SEQ ID NO 4
<211> LENGTH: 13
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 4
tcgnntcgnn tcg                                               13
```

COMPOSITIONS AND METHODS FOR TREATING VIRAL INFECTIONS THROUGH STIMULATED INNATE IMMUNITY IN COMBINATION WITH ANTIVIRAL COMPOUNDS

This application claims priority to U.S. Provisional Applications 62/053,013 filed Sep. 19, 2014 and 62/053,610 filed Sep. 22, 2014. Each of which is incorporated herein by reference in its entirety.

STATEMENT REGARDING FEDERALLY FUNDED RESEARCH

This invention was made with government support under grant number 1R43HL118926-01A1, 1DP2HL123229-01, and 1R01HL117976-01A1 awarded by the National Heart Lung and Blood Institute or the National Institutes of Health. The government has certain rights in the invention.

BACKGROUND OF THE INVENTION

I. Field of the Invention

The present invention relates generally to the fields of virology, immunology, and antimicrobial pharmacotherapy. More particularly the compositions and methods of the invention related to increasing the resistance of an individual to viral infection.

II. Background

The susceptibility of the lungs to infection arises from the architectural requirements of gas exchange. To support ventilation, humans continuously expose about 80 m² lung surface area to the external environment. Lungs are exposed not only to air, but also the particles, droplets, and pathogens that are suspended in the air. Unlike cutaneous surfaces that are wrapped in impermeable skin or the gastrointestinal tract with a thick adsorbent blanket of mucus, the lungs present a large environmental interface with a minimal barrier defense. A more substantial barrier is precluded by the demand for unimpeded gaseous diffusion.

Despite their structural vulnerability, the lungs generally defend themselves successfully against infection through a variety of mechanical, humoral, and cellular mechanisms (Knowles et al., 2002; Martin and Frevert, 2005; Rogan, et al., 2006; Travis, et al., 2001); (Mizgerd, 2008; Bals and Hiemstra, 2004; Bartlett et al., 2008; Hiemstra, 2007; Hippenstiel et al., 2006; Schutte and McCray, 2002). Most inhaled microbial pathogens fail to penetrate to the alveoli due to impaction against the airway walls, where they are entrapped by mucus and then expelled via the mucociliary escalator system (Knowles et al., 2002). For those pathogens that escape this fate, the constitutive presence of antimicrobial peptides in the airway lining fluid limits their growth (Rogan, et al., 2006; Travis, et al., 2001). Alveolar macrophages that reside in the most distal airspaces are able to ingest these organisms, thereby clearing the lungs from a potential infection.

Though often regarded as passive gas exchange barriers, the airway and alveolar epithelia supplement the baseline lung defenses by undergoing remarkable local structural and functional changes when pathogenic stimuli are encountered. In response to viral, fungal, or allergic inflammation, airway secretory cells rapidly increase their height and fill their apical cytoplasm with secretory granules, a process termed inflammatory metaplasia (Evans et al., 2004; Williams et al., 2006). In the presence of pathogens, the alveolar epithelia activate their plasmalemmal systems and secretory machinery, thereby engaging leukocytes in lung protection (Evans et al., 2005). Perhaps most importantly, microbial interactions with respiratory epithelial pattern recognition receptors causes numerous microbicidal products to be expressed into the airway lining fluid, including defensins, cathelicidins, lysozyme, and reactive oxygen species (Rogan et al., 2006; Forteza et al., 2005; Akinbi et al., 2000; Bals 15 and Hiemstra, 2004; Bals and Hiemstra, 2006). It is of note that pneumonia (bacterial or viral) is the leading cause of death from infection worldwide.

There is a need for additional methods and compositions for inhibiting and/or treating viral infections.

SUMMARY

Certain embodiments are directed to compositions and methods for treating viral infections. In certain aspects the viral infection is a viral infection of the lungs. Other embodiments are directed to delivery devices containing an anti-viral composition(s). In certain aspects the delivery devices contain a formulation with activity against a broad spectrum of viruses. In a further aspect a delivery device can contain a formulation comprising one or more anti-viral drugs that target a specific family of viruses. Studies have shown that the combination treatments described herein are mechanism independent and that administration of a lipopeptide(s) and immune stimulatory oligonucleotide(s) can be co-administered or combined with a variety of antivirals having a variety of therapeutic mechanisms and targets. Thus, lipopeptide/oligonucleotide compositions and treatments can be effectively combined with wide variety of antivirals and are not limited to any particular antiviral.

Certain embodiments are directed to compositions that increase resistance of a subject to viruses when administered to the subject. Additional embodiments are directed to methods of using such compositions to attenuate viral infection in the subject. Thus, embodiments include, but are not limited to compositions, formulations, and methods for the enhancement of a mammalian (e.g., a human) subject's biological defenses against viral infection. In certain aspects compositions are administered or deposited in an effective amount in the lungs of a subject. In certain aspects the compositions and methods provide a rapid and temporal increase in resistance to infection and/or augmentation of biological defenses against viral infection. Attenuation of viral infection can be by inhibiting, treating, or preventing virus infection or replication or survival. In specific embodiments the subject is a human patient.

Aspects described here increase resistance to infection and enhance the defenses of the lung and respiratory tract of a subject. A subject administered a composition described herein is afforded a therapeutic, prophylactic, or therapeutic and prophylactic response to a potentially infecting virus.

Certain embodiments are directed to formulations or co-formulations of active components to provide for an anti-viral effect. In certain aspects a co-formulation comprises one or more (a) lipopeptide(s), (b) immune stimulatory oligonucleotide(s), or (c) antiviral drug(s). In certain aspects the anti-viral compositions contain an effective amount of at least one, two, or three of the following: (a) lipopeptide, (b) stimulatory oligonucleotide, or (c) antiviral drug(s). In certain aspects one or more lipopeptides can be included in a formulation. In a further aspect one or more stimulatory oligonucleotides can be included in a formulation. In still a further aspect one or more anti-viral drugs can be included in a formulation. The term stimulatory oligonucleotide and immune stimulatory oligonucleotide are used interchangeably to refer to an immune stimulatory oligonucleotide. In certain aspects the lipopeptide and stimulatory oligonucleotide are co-formulated or administered simultaneously, i.e. lipopeptide/stimulatory oligonucleotide co-administration. In a further aspect the lipopeptide/stimulatory oligonucleotide co-administration is administered in conjunction with administration of an additional antiviral drug or therapy. "Administered in conjunction" or "coadministration" as used herein refers to administration of two or more active agents in a manner that will allow them to be present together in-vivo for period of time. Accordingly, while the term "coadministration" includes simultaneous administration of two or more active agents, and administration from a single formulation, it is to be understood that it is not limited thereto.

In certain aspects a lipopeptide is selected from diacyl and triacyl lipopeptides. In certain aspects a lipopeptide is FSL-1; Pam3Cys (tripalmitoyl-S-glyceryl cysteine); S-[2,3-bis (palmitoyloxy)-(2RS)-propyl]-N-palmitoyl-(R)-cysteine; (S-[2,3-bis(palmitoyloxy)-(2-R,S)-propyl]-Npalmitoyl-(R)-Cys-(S)-Ser-(Lys)4-hydroxytrihydrochloride; Pam3Cys-Ser-Ser-Asn-Ala; PaM3Cys-Ser-(Lys)4; Pam3Cys-Ala-Gly; Pam3Cys-Ser-Gly; Pam3Cys-Ser; PaM3Cys-OMe; Pam3 Cys-OH; PamCAG (palmitoyl-Cys((RS)-2,3-di(palmitoyloxy)-propyl)-Ala-Gly-OH); or Pam2CSK4 (PaM2CSK4, dipalmitoyl-S-glyceryl cysteine-serine-(lysine)4); Pam2Cys-Ser-(Lys)4). In certain aspects the lipopeptide is PAM2CSK4.

In certain aspects a stimulatory oligonucleotide is a type A, B, or C oligodeoxynucleotide (ODN). In certain aspects the stimulatory oligonucleotide is a type C ODN. In a further aspect the ODN is ODN2395 (tcgtcgttttcggcgcgcgccg (SEQ ID NO:1) or ODNM362 (tcgtcgtcgttcgaacgacgttgat (SEQ ID NO:2) or ODN10101 (tcgtcgttttcgcgcgcgccg (SEQ ID NO:3).

In certain aspects an antiviral drug is a drug that effects the biology of a virus and attenuates or inhibits attachment, entry, replication, shedding, latency or a combination thereof. In a further aspect the antiviral drug can be a viral mimetic, a nucleotide analog, a sialidase inhibitor, or a protease inhibitor. In certain aspects the anti-viral drug is a neuraminidase inhibitor or nucleotide analog. In a particular aspect the anti-viral drug is amantadine, rimantadine, ribavirin, zanamivir, or oseltamivir. In certain aspects the antiviral drug is a small molecule, or an antibody or antibody fragment.

In certain embodiments the lipopeptide is PAM2CSK4; the stimulatory oligonucleotide is ODN2395 (tcgtcgttttcggcgcgcgccg (SEQ ID NO:1) or ODNM362 (tcgtcgtcgttcgaacgacgttgat (SEQ ID NO:2) or ODN10101 (tcgtcgttttcgcgcgcgccg (SEQ ID NO:3); and the antiviral drug is amantadine, rimantadine, ribavirin, zanamivir, or oseltamivir.

In one embodiment, the anti-viral compositions contain about 0.1, 0.5, 1, 5, or 10% to about 1, 5, 10, or 20% by weight of at least one of (a) lipopeptide(s), (b) stimulatory oligonucleotide(s), or (c) antiviral drug(s).

In certain aspects a formulation can comprise a lipopeptide in an amount that is at least, less than or about 0.1, 1, 5, 10, 15, 20, 25, 30, 35, 40, 45, 50, or 55% by weight or volume (or any range derivable therein).

In certain aspects a formulation can comprise a stimulatory oligonucleotide in an amount that is at least, less than or about 0.1, 1, 5, 10, 15, 20, 25, 30, 35, 40, 45, 50, or 55% by weight or volume (or any range derivable therein).

In certain aspects a formulation can comprise an anti-viral drug in an amount that is at least, less than or about 0.1, 1, 5, 10, 15, 20, 25, 30, 35, 40, 45, 50, or 55% by weight or volume (or any range derivable therein).

In one embodiment, the antiviral compositions contain at least one of (a) lipopeptide, (b) stimulatory oligonucleotide, or (c) antiviral drug(s). In another embodiment, the anti-viral compositions contain at least two (a) lipopeptide, (b) stimulatory oligonucleotide, or (c) antiviral drug(s). In still another embodiment the anti-viral compositions contain a (a) lipopeptide, (b) stimulatory oligonucleotide, and (c) antiviral drug(s).

In one embodiment, the weight ratio of (a) lipopeptide, (b) stimulatory oligonucleotide, or (c) antiviral drug(s) relative to each other in the anti-viral compositions includes or is at least or at most 0, 1, 2, 3, 4, 5, 6, 7, 8, 9, 10 parts lipopeptide (or any range derivable therein) to, to at least, or to at most 0, 1, 2, 3, 4, 5, 6, 7, 8, 9, 10 parts stimulatory oligonucleotide (or any range derivable therein) to, to at least or to at most 0, 1, 2, 3, 4, 5, 6, 7, 8, 9, 10 parts anti-viral drug (or any range derivable therein). In certain aspects a formulation can comprise about 4 parts lipopeptide, about 1 part stimulatory oligonucleotide. In additional embodiments, there is also about or at least about, or at most about 1, 2, 3, 4, 5, 6, 7, 8, 9, or 10 parts antiviral drug (or any range derivable therein).

In certain embodiments a composition can comprise, comprise at least or comprise at most 0, 0.01, 0.05, 0.1, 0.5, 1, 1.5, 2.0, 2.5, 3.0, 3.5, 4.0, 4.5, 5.0, 10 g of lipopeptide (or any range derivable therein) per 1, 5, or 10 mL; 0, 0.01, 0.05, 0.1, 0.5, 1, 1.5, 2.0, 2.5, 3.0, 3.5, 4.0, 4.5, 5.0, 10 g of stimulatory oligonucleotide (or any range derivable therein) per 1, 5, or 10 mL; and/or 0, 0.01, 0.05, 0.1, 0.5, 1, 1.5, 2.0, 2.5, 3.0, 3.5, 4.0, 4.5, 5.0, 10, 50 up to 100 g of antiviral drug(s) (or any range derivable therein) per 1, 5, or 10 mL.

Certain embodiments are directed to methods of treating, inhibiting, or attenuating a viral infection in a subject who has or is at risk for developing such an infection. The methods comprising administering an effective amount of an anti-viral composition described herein.

In certain embodiments a lipopeptide and stimulatory oligonucleotide can be administered via the respiratory system and an anti-viral drug can be administered orally or intravascularly.

Certain embodiments are directed to compositions capable of being administered to the respiratory tract 1, 2, 3, 4, or more times a day, week, or month (or any combination derivable therein).

In other aspects a composition is administered in a nebulized formulation. The (a) lipopeptide, (b) stimulatory oligonucleotide, or (c) antiviral drug(s) can be administered in an amount, selected independently for each component, from about, about at least or about at most 0.1, 1, 5, 10, 50 μg or mg/kg to about, about at least or about at most 5, 10, 50, 100 μg or mg/kg of the subject's body weight, including all values and ranges there between.

Compositions described herein can be administered via the respiratory tract. Methods of the invention include the administration of a composition by inhalation or other methods of administration to the upper and/or lower respiratory tract. In certain aspects, the anti-viral composition is administered in a nebulized or aerosolized formulation. In a further aspect the composition is aerosolized or nebulized or in a form that can be inhaled by or instilled in a subject. The composition can be administered by inhalation or inspiration. The anti-viral composition, including (a) lipopeptide, (b) stimulatory oligonucleotide, or (c) antiviral drug(s), can be administered in an amount of from about, or at least or at most about, 0.01, 0.05, 0.1, 25 0.5, 1, 5, 10, 15, 20, 25, 30, 35, 40, 45, 50, 55, 60, 65, 70 µg or mg/kg (or any range derivable therein) to about, or at least or at most about, 55, 60, 65, 70, 75, 80, 85, 90, 95, 100, 125, 150, 200 µg or mg/kg (or any range derivable therein) of the subject's body weight. In other aspects, a subject can be administered about, or at least or at most about 0.01, 0.05, 0.1, 0.5, 1, 5, 10, 15, 20, 25, 30, 35, 40, 45, 50, 55, 60, 65, 70, 75, 80, 85, 90, 95, 100, 125, 150, 200 µg or mg (or any range derivable therein) of (a) lipopeptide, (b) stimulatory oligonucleotide, or (c) antiviral drug(s) individually or in combination (total amount). The subject can be at risk of exposure to or exposed to a virus. Still further embodiments include methods where the composition is administered before; after; during; before and after; before and during; during and after; before, after, and during exposure or suspected exposure or heightened risk of exposure to the virus. The subject can be exposed to a bioweapon or to an opportunistic pathogen. In particular aspects the subject is immunocompromised, such as an infant, a cancer patient, or an AIDS patient. In certain aspects the subject is located in an area having or at risk of having a viral outbreak.

Certain embodiments include a pharmaceutical composition comprising or consisting essentially of PAM2CSK4, ODNM362, and optionally an antiviral agent, that is formulated for aerosolized or nebulized delivery. In certain embodiments the antiviral agent is ribavirin or oseltamivir. Methods include treating a patient for a virus infection comprising administering to the patient effective amounts of PAM2CSK4 and ODNM362, and optionally administering an antiviral agent, wherein the PAM2CSK4 and ODNM362 are administered to the patient as an aerosol or with a nebulizer. In certain embodiments, treatment of the virus infection does not include an active agent other than a lipopeptide, a stimulatory oligonucleotide (such as a Class C ODN, including ODNM362), and an antiviral drug. In certain aspects the compositions or methods specifically exclude an antigen or immunogen targeting a specific virus or group viruses.

In certain aspects the virus is an Adenoviridae, Coronaviridae, Filoviridae, Flaviviridae, Hepadnaviridae, Herpesviridae, Orthomyxoviridae, Paramyxovirinae, Pneumovirinae, Picornaviridae, Poxyiridae, Retroviridae, or Togaviridae virus. In a further aspect a virus is Parainfluenza, Influenza (seasonal, swine, avian, etc.), Marburg, Ebola, Severe acute respiratory syndrome coronavirus, Yellow fever virus, Human respiratory syncytial virus, Hantavirus, measles, MERS, rhinovirus, human metapneumovirus, or Vaccinia virus. In other aspects the virus is influenza, RSV, or parainfluenza virus. In a further aspect the virus can be a Severe acute respiratory syndrome coronovirus (SARS-COV) or Middle Eastern Respiratory Syndrome coronavirus (MERS-COV).

The terms "attenuating," "inhibiting," "reducing," or "prevention," or any variation of these terms, when used in the claims and/or the specification includes any measurable decrease or complete inhibition to achieve a desired result, e.g., reduction in post-exposure viral survival, load, or growth.

As used herein, "an effective amount" means the concentration or quantity or level of the active compound(s) of the present invention that can attain a particular medical end, such as control or destruction of virally-infected cells or viruses, without producing unacceptable toxic symptoms. The term "effective amount" also refers to the quantity of an active compound(s) that is sufficient to yield a desired therapeutic response without undue adverse side effects (such as toxicity, irritation, or allergic response) commensurate with a reasonable benefit/risk ratio when used in the manner of this invention. The specific "effective amount" can vary with such factors as the particular condition being treated, the physical condition of the patient, the type of mammal being treated, the duration of the treatment, the nature of concurrent therapy (if any), and the specific formulations employed.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
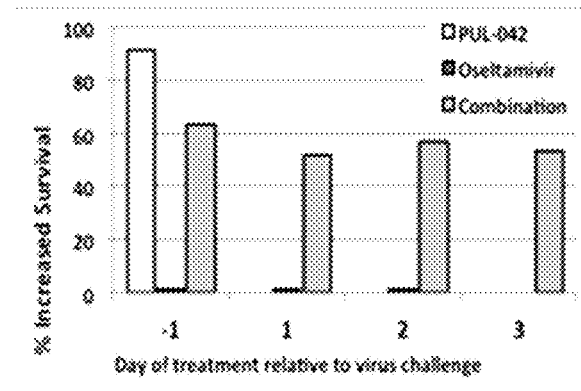
FIG. 1. Effect of PUL-042 on percent survival compared to untreated control mice following lethal challenge of influenza infection. The x-axis indicates the day on which PUL-042 and/or oseltamivir was administered relative to influenza infection.
Figure 2:
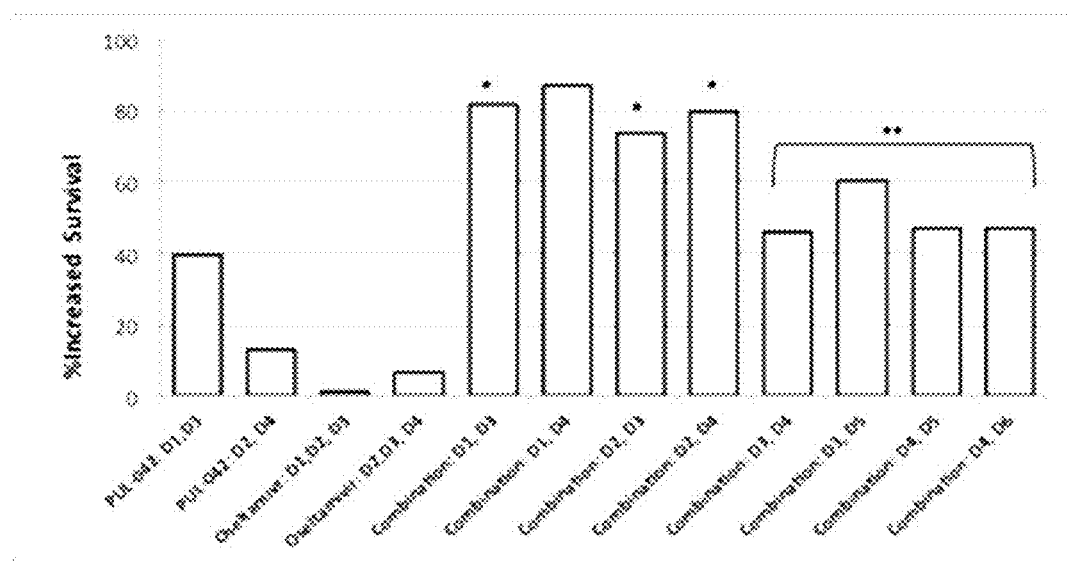
FIG. 2. Effect of timing of multiple doses of combination treatment with PUL-042 and oseltamivir on survival of a lethal influenza challenge. The x-axis indicates the day of initiation of treatment and timing of subsequent treatments relative to the influenza challenge. * Statistically significant difference from untreated controls.  Combined results of treatments starting at D3 or D4, Ave.=49.8%, P<0.001. * Combination D1 and D4, while a strong result, was performed only once and statistical significance was not determined.
Figure 3:
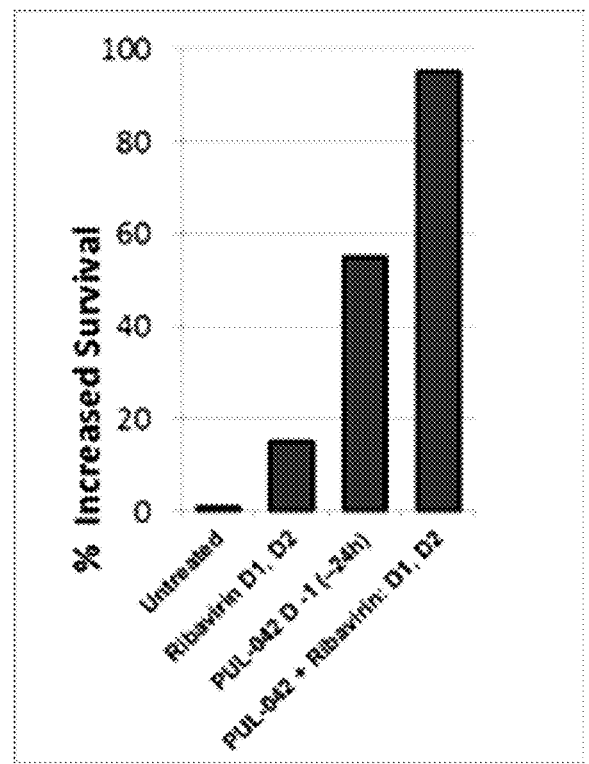
FIG. 3. Effect of PUL-042 combination treatment with ribavirin on survival of a lethal influenza challenge. Initiating treatment on D1 after infection increased the percent survival to 95% compared to untreated controls.
Figure 4:
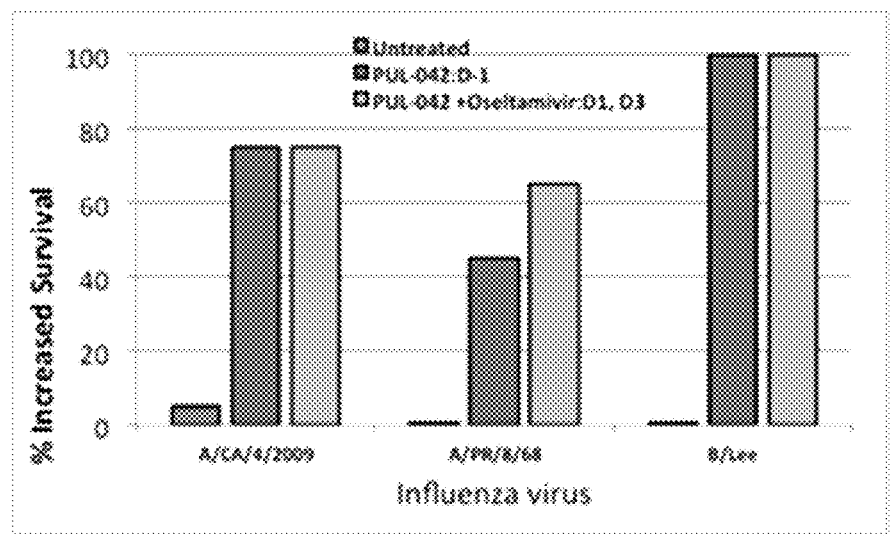
FIG. 4. Effect of PUL-042 on percent survival following lethal challenge of three influenza viruses. Fifteen outbred NIH Swiss-Webster mice were used in each group. The x-axis indicates the day on which PUL-042 and/or oseltamivir was administered relative to infection challenge.

The immune system is the system of specialized cells and organs that protect an organism from outside biological influences. When the immune system is functioning properly, it protects the body against microbial infections, and destroys cancer cells and foreign substances. If the immune system weakens, its ability to defend the body also weakens, allowing pathogens to grow in the body.

The immune system is often divided into: (a) an innate immunity comprised of components that provide an immediate "first-line" of defense to continuously ward off pathogens and (b) an adaptive (acquired) immunity comprising the production of antibodies and production or stimulation of T-cells specifically designed to target particular pathogens. Using adaptive immunity the body can develop over time a specific immunity to particular pathogen(s). This response takes days to develop, and so is not effective at preventing an initial invasion, but it will normally prevent any subsequent infection, and also aids in clearing up longer-lasting infections.

In response to certain inflammatory stimuli, the secretory cells of the airway epithelium of mice and humans rapidly undergo a remarkable change in structure termed inflammatory metaplasia. Most of the structural changes can be ascribed to increased production of secreted, gel-forming mucins, while additional macromolecules with functions in mucin secretion, microbial killing or inflammatory signaling are also upregulated. The physiologic function of this response is thought to be augmentation of local defenses against microbial and helminthic pathogens, although that hypothesis has received only limited formal testing. Paradoxically, excessive production and secretion of gel-forming mucins is a major cause of airflow obstruction in common inflammatory diseases of the airways such as asthma, cystic fibrosis, and chronic obstructive pulmonary disease (COPD). The stimulation of innate immunity without the production or with the reduced production of mucin provides an additional method of attenuating infection of the respiratory tract by preventing and/or treating a viral infection of a subject.

III. Anti-Viral Compositions and Treatments

The compositions and methods of the present invention may be used in the context of a number of therapeutic or prophylactic applications. In order to increase the effectiveness of a treatment with the compositions described or to augment the protection of another therapy (second therapy), e.g., vaccination or antimicrobial therapy, it may be desirable to combine these compositions and methods with other agents and methods effective in the treatment, reduction of risk of infection, or prevention of diseases and pathologic conditions, for example, anti-viral treatments. In certain aspects a plurality of components are formulated in a composition for administration to a subject in need of such.

Administration of a composition described to a subject will follow general protocols for the administration via the respiratory system, and the general protocols for the administration of a particular secondary therapy will also be followed, taking into account the toxicity, if any, of the treatment. It is expected that the treatment cycles would be repeated as necessary. It also is contemplated that various standard therapies, as well as vaccination, may be applied in combination with the described therapies.

In certain embodiments a composition can comprise one or more of (a) lipopeptide, (b) stimulatory oligonucleotide, and/or (c) anti-viral drug(s), in various combinations. Combination being in the form of co-formulation or alternatively co-administration of components.

A. Lipopeptides

Lipopeptides include synthetic triacylated and diacylated lipopeptides. The peptide component can include single amino acids such as cysteine or short 2, 3, 4, 5, 6, 7, 8, 9, or 10 amino acid peptides. In certain aspects the peptide can include one or more amino terminal serine and 1, 2, 3, 4, or more carboxy terminal asparagine, glycine, alanine, lysine residues or combinations thereof. A nonlimiting example of lipopeptide is FSL-1 (a synthetic lipoprotein derived from *Mycoplasma salivarium* 1), Pam3Cys (tripalmitoyl-S-glyceryl cysteine)S-[2,3-bis(palmitoyloxy)-(2RS)-propyl]-N-palmitoyl-(R)-cysteine, where "Pam3" is "tripalmitoyl-Sglyceryl") (Aliprantis et al., 1999), derivatives of Pam3Cys (S-[2,3-bis(palmitoyloxy)-(2-R,S)-propyl]-Npalmitoyl-(R)-Cys-(S)-Ser-(Lys)4-hydroxytrihydrochloride; Pam3Cys-Ser-Ser-Asn-Ala; PaM3Cys-Ser-(Lys)4; Pam3Cys-Ala-Gly; Pam3Cys-Ser-Gly; Pam3Cys-Ser; PaM3Cys-OMe; Pam3 Cys-OH; PamCAG, palmitoyl-Cys((RS)-2,3-di(palmitoyloxy)-propyl)-Ala-Gly-OH; Pam2CSK4 (PaM2CSK4, dipalmitoyl-S-glyceryl cysteine-serine-(lysine)4), Pam2Cys-Ser-(Lys)4); and the like. Synthetic lipopeptides have been described in the literature. See, e.g., Kellner et al. (1992); Seifer et al. (1990); Lee et al. (2003).

B. Stimulatory Oligonucleotide

Stimulatory oligonucleotides include nucleic acids comprising the sequence 5'-CG-3' (a "CpG nucleic acid"), in certain aspects C is unmethylated. The terms "polynucleotide," and "nucleic acid," as used interchangeably herein in the context of stimulatory oligonucleotides molecules, refer to a polynucleotide of any length, and encompasses, inter alia, single- and double-stranded oligonucleotides (including deoxyribonucleotides, ribonucleotides, or both), modified oligonucleotides, and oligonucleosides, alone or as part of a larger nucleic acid construct, or as part of a conjugate with a non-nucleic acid molecule such as a polypeptide.

Thus a stimulatory oligonucleotide may be, for example, single-stranded DNA (ssDNA), double-stranded DNA (dsDNA), single-stranded RNA (ssRNA) or double-stranded RNA (dsRNA).

A stimulatory oligonucleotide may comprise at least one nucleoside comprising an L-sugar. The L-sugar may be deoxyribose, ribose, pentose, deoxypentose, hexose, deoxyhexose, glucose, galactose, arabinose, xylose, lyxose, or a sugar "analog" cyclopentyl group. The L-sugar may be in pyranosyl or furanosyl form.

Stimulatory oligonucleotides generally do not provide for, nor is there any requirement that they provide for, expression of any amino acid sequence encoded by the polynucleotide, and thus the sequence of a stimulatory oligonucleotide may be, and generally is, non-coding. Stimulatory oligonucleotide may comprise a linear double or single-stranded molecule, a circular molecule, or can comprise both linear and circular segments. Stimulatory oligonucleotide may be single-stranded, or may be completely or partially double-stranded.

In some embodiments, a stimulatory oligonucleotide for use in a subject method is an oligonucleotide, e.g., consists of a sequence of from about 5 nucleotides to about 200 nucleotides, from about 10 nucleotides to about 100 nucleotides, from about 12 nucleotides to about 50 nucleotides, from about 15 nucleotides to about 25 nucleotides, from 20 nucleotides 15 to about 30 nucleotides, from about 5 nucleotides to about 15 nucleotides, from about 5 nucleotides to about 10 nucleotides, or from about 5 nucleotides to about 7 nucleotides in length. In some embodiments, a stimulatory oligonucleotide that is less than about 15 nucleotides, less than about 12 nucleotides, less than about 10 nucleotides, or less than about 8 nucleotides in length is associated with a larger molecule.

In general, a stimulatory oligonucleotide used in a subject composition comprises at least one unmethylated CpG motif. The relative position of any CpG sequence in a polynucleotide in certain mammalian species (e.g., rodents) is 5'-CG-3'(i.e., the C is in the 5' position with respect to the G in the 3' position).

In some embodiments, a stimulatory oligonucleotide comprises a central palindromic core sequence comprising at least one CpG sequence, where the central palindromic core sequence contains a phosphodiester backbone, and where the central palindromic core sequence is flanked on one or both sides by phosphorothioate backbone-containing polyguanosine sequences.

In other embodiments, a stimulatory oligonucleotide comprises one or more TCG sequences at or near the 5' end of the nucleic acid; and at least two additional CG dinucleotides. In some of these embodiments, the at least two additional CG dinucleotides are spaced three nucleotides, two nucleotides, or one nucleotide apart. In some of these embodiments, the at least two additional CG dinucleotides are contiguous with one another. In some of these embodiments, the stimulatory oligonucleotide comprises (TCG)n, where n=1 to 3, at the 5' end of the nucleic acid. In other embodiments, the stimulatory oligonucleotide comprises (TCG)n, where n=1 to 3, and where the (TCG)n sequence is flanked by one nucleotide, two nucleotides, three nucleotides, four nucleotides, or five nucleotides, on the 5' end of the (TCG)n sequence.

Exemplary consensus CpG motifs useful in the invention include, but are not necessarily limited to: 5'-Purine-Purine-(C)-(G)-Pyrimidine-Pyrimidine-3', in which the stimulatory oligonucleotide comprises a CpG motif flanked by at least two purine nucleotides (e.g., GG, GA, AG, AA, II, etc.,) and at least two pyrimidine nucleotides (CC, TT, CT, TC, UU, etc.); 5'-Purine-TCG-Pyrimidine-Pyrimidine-3; 5'-TCG-N-N-3; where N is any base; 5'-Nx(CG)nNy, where N is any base, where x and y are independently any integer from 0 to 200, e.g., 0, 1, 2, 3, 4, 5, 6, 7, 8, 9, 10, 11-15, 16-20, 21-25, 25-30, 30-50, 50-75, 75-100, 100-150, or 150-200; and n is any integer that is 1 or greater, e.g., 1, 2, 3, 4, 5, 6, 7, 8, 9, 10, or greater. 5'-Nx(TCG)nNy, where N is any base, where x and y are independently any integer from 0 to 200, e.g., 0, 1, 2, 3, 4, 5, 6, 7, 8, 9, 10, 11-15, 16-20, 21-25, 25-30, 30-50, 50-75, 75-100, 100-150, or 150-200; and n is any integer that is 1 or greater, e.g., 1, 2, 3, 4, 5, 6, 7, 8, 9, 10, or greater. 5'-(TCG)n-3', where n is any integer that is 1 or greater, e.g., to provide a TCG-based TLR9 ligand (e.g., where n=3, the polynucleotide comprises the sequence 5'TCGNNTCGNNTCG-3; SEQ ID NO:4); 5 Nm-(TCG)n-Np-3', where N is any nucleotide, where m is zero, one, two, or three, where n is any integer that is 1 or greater, and where p is one, two, three, or four; 5 Nm-(TCG)n-Np-3', where N is any nucleotide, where m is zero to 5, and where n is any integer that is 1 or greater, where p is four or greater, and where the sequence N-N-N-N comprises at least two CG dinucleotides that are either contiguous with each other or are separated by one nucleotide, two nucleotides, or three nucleotides; and 5'Purine-Purine-CG-Pyrimidine-TCG-3'.

Where a stimulatory oligonucleotide comprises a sequence of the formula: 5'-Nm(TCG)n-Np-3', where N is any nucleotide, where m is zero to 5, and where n is any integer that is 1 or greater, where p is four or greater, and where the sequence N-N-N-N comprises at least two CG dinucleotides that are either contiguous with each other or are separated by one nucleotide, two nucleotides, or three nucleotides, exemplary stimulatory oligonucleotide useful in the invention include, but are not necessarily limited to: (1) a sequence of the formula in which n=2, and Np is NNCGNNCG; (2) a sequence of the formula in which n=2, and Np is AACGTTCG; (3) a sequence of the formula in which n=2, and Np is TTCGAACG; (4) a sequence of the formula in which n=2, and Np is TACGTACG; (5) a sequence of the formula in which n=2, and Np is A TCGA TCG; (6) a sequence of the formula in which n=2, and Np is CGCGCGCG; (7) a sequence of the formula in which n=2, and Np is GCCGGCCG; (8) a sequence of the formula in which n=2, and Np is CCCGGGCG; (9) a sequence of the formula in which n=2, and Np is GGCGCCCG; (10) a sequence of the formula in which n=2, and Np is CCCGTTCG; (11) a sequence of the formula in which n=2, and Np is GGCGTTCG; (12) a sequence of the formula in which n=2, and Np is TTCGCCCG; (13) a sequence of the 30 formula in which n=2, and Np is TTCGGGCG; (14) a sequence of the formula in which n=2, and Np is AACGCCCG; (15) a sequence of the formula in which n=2, and Np is AACGGGCG; (16) a sequence of the formula in which n=2, and Np is CCCGAACG; and (17) a sequence of the formula in which n=2, and Np is GGCGAACG; and where, in any of 1-17, m=zero, one, two, or three.

Where a nucleic acid TLR9 ligand comprises a sequence of the formula: 5'Nm(TCG)n-Np-3', where N is any nucleotide, where m is zero, one, two, or three, where n is any integer that is 1 or greater, and where p is one, two, three, or four, exemplary TLR9 ligands useful in the invention include, but are not necessarily limited to: (1) a sequence of the formula where m=zero, n=1, and Np is T-T-T; (2) a sequence of the formula where m=zero, n=1, and Np is T-T-T-T; (3) a sequence of the formula where m=zero, n=1, and Np is C-C-CC; (4) a sequence of the formula where m=zero, n=1, and Np is A-A-A-A; (5) a sequence of the formula where m=zero, n=1, and Np is A-G-A-T; (6) a sequence of the formula where Nm is T, n=1, and Np is T-T-T; (7) a sequence of the formula where Nm is A, n=1, and Np is T-T-T; (8) a sequence of the formula where Nm is C, n=1, and Np is T-T-T; (9) a sequence of the formula where Nm is G, n=1, and Np is T-T-T; (10) a sequence of the formula where Nm is T, n=1, and Np is A-T-T; (11) a sequence of the formula where Nm is A, n=1, and Np is A-T-T; and (12) a sequence of the formula where Nm is C, n=1, and Np is A-T-T.

Stimulatory oligonucleotides useful in the invention include, but are not necessarily limited to, polynucleotides comprising one or more of the following nucleotide sequences: AGCGCT, AGCGCC, AGCGTT, AGCGTC, AACGCT, AACGCC, AACGTT, AACGTC, GGCGCT, GGCGCC, GGCGTT, GGCGTC, GACGCT, GACGCC, GACGTT, GACGTC, GTCGTC, GTCGCT, GTCGTT, GTCGCC, ATCGTC, ATCGCT, ATCGTT, ATCGCC, TCGTCG, or TCGTCGTCG.

Additional stimulatory oligonucleotides useful in the invention include, but are not necessarily limited to, polynucleotides comprising one or more of the following nucleotide sequences: TCGXXXX, TCGAXXX, XTCGXXX, XTCGAXX, TCGTCGA, TCGACGT, TCGAACG, TCGAGAT, TCGACTC, TCGAGCG, TCGATTT, TCGCTTT, TCGGTTT, TCGTTTT, TCGTCGT, ATCGATT, TTCGTTT, TTCGATT, ACGTTCG, AACGTTC, TGACGTT, TGTCGTT, TCGXXX, TCGAXX, TCGTCG, AACGTT, ATCGAT, GTCGTT, GACGTT, TCGXX, TCGAX, TCGAT, TCGTT, TCGTC, TCGA, TCGT, TCGX, and TCG (where "X" is any nucleotide).

Stimulatory oligonucleotides useful in the invention include, but are not necessarily limited to, polynucleotides comprising the following octameric nucleotide sequences: AGCGCTCG, AGCGCCCG, AGCGTTCG, AGCGTCCG, AACGCTCG, AACGCCCG, AACGTTCG, AACGTCCG, GGCGCTCG, GGCGCCCG, GGCGTTCG, GGCGTCCG, GACGCTCG, GACGCCCG, GACGTTCG, and GACGTCCG.

A stimulatory oligonucleotide useful in carrying out a subject method can comprise one or more of any of the above CpG motifs. For example, a stimulatory oligonucleotide useful in the invention can comprise a single instance or multiple instances (e.g., 2, 3, 4, 5 or more) of the same CpG motif. Alternatively, a stimulatory oligonucleotide can comprise multiple CpG motifs (e.g., 2, 3, 4, 5 or more) where at least two of the multiple CpG motifs have different consensus sequences, or where all CpG motifs in the stimulatory oligonucleotides have different consensus sequences.

A stimulatory oligonucleotide useful in the invention may or may not include palindromic regions. If present, a palindrome may extend only to a CpG motif, if present, in the core hexamer or octamer sequence, or may encompass more of the hexamer or octamer sequence as well as flanking nucleotide sequences.

In some embodiments, a stimulatory oligonucleotide is multimeric. A multimeric stimulatory oligonucleotide comprises two, three, four, five, six, seven, eight, nine, ten, or more individual (monomeric) stimulatory oligonucleotides, as described above, linked via noncovalent bonds, linked via covalent bonds, and either linked directly to one another, or linked via one or more spacers. Suitable spacers include nucleic acid and non-nucleic acid molecules, as long as they are biocompatible. In some embodiments, multimeric stimulatory oligonucleotide comprises a linear array of monomeric stimulatory oligonucleotides. In other embodiments, a multimeric stimulatory oligonucleotide is a branched, or dendrimeric, array of monomeric stimulatory oligonucleotides.

Stimulatory oligonucleotide modifications. A stimulatory oligonucleotide suitable for use in a subject composition can be modified in a variety of ways. For example, a stimulatory oligonucleotide can comprise backbone phosphate group modifications (e.g., methylphosphonate, phosphorothioate, phosphoroamidate and phosphorodithioate internucleotide linkages), which modifications can, for example, enhance their stability in vivo, making them particularly useful in therapeutic applications. A particularly useful phosphate group modification is the conversion to the phosphorothioate or phosphorodithioate forms of a stimulatory oligonucleotide. Phosphorothioates and phosphorodithioates are more resistant to degradation in vivo than their unmodified oligonucleotide counterparts, increasing the half-lives of the stimulatory oligonucleotides and making them more available to the subject being treated.

Other modified stimulatory oligonucleotides encompassed by the present invention include stimulatory oligonucleotides having modifications at the 5' end, the 3' end, or both the 5' and 3' ends. For example, the 5' and/or 3' end can be covalently or non-covalently associated with a molecule (either nucleic acid, non-nucleic acid, or both) to, for example, increase the bio-availability of the stimulatory oligonucleotide, increase the efficiency of uptake where desirable, facilitate delivery to cells of interest, and the like.

The terms "CpG-ODN," "CpG nucleic acid," "CpG polynucleotide," and "CpG oligonucleotide," used interchangeably herein, refer to a polynucleotide that comprises at least one 5'-CG-3' moiety, and in many embodiments comprises an unmethylated 5'-CG-3' moiety. In general, a CpG nucleic acid is a single- or double-stranded DNA or RNA polynucleotide having at least six nucleotide bases that may comprise, or consist of, a modified nucleotide or a sequence of modified nucleosides. In some embodiments, the 5'-CG-3' moiety of the CpG nucleic acid is part of a palindromic nucleotide sequence. In some embodiments, the 5'-CG-3' moiety of the CpG nucleic acid is part of a non-palindromic nucleotide sequence.

C. Anti-Viral Drugs.

In certain aspects an anti-viral drug(s) may be used in combination with or as a component of an anti-viral composition (co-formulated with other components) described herein. Anti-viral drugs are a class of medication used specifically for treating viral infections and they should be distinguished from viricides, which actively deactivate virus particles outside the body. Most of the antivirals now available are designed to help deal with HIV, herpes viruses, the hepatitis B and C viruses, and influenza A and B viruses. Anti-viral agents useful in embodiments include, but are not limited to, immunoglobulins, amantadine, interferons, nucleotide analogues, sialidase inhibitors and protease inhibitors. It is contemplated that one or more of these may be included in embodiments or they may be excluded from embodiments. In certain embodiments, the antiviral drug is one that inhibits the virus directly, instead of destroying or killing the virus. In other embodiments, an antiviral drug is not an immunoglobulin or agent that involves the immune system.

One anti-viral strategy is to interfere with the ability of a virus to infiltrate a target cell. This stage of viral replication can be inhibited by using agents that mimic the virus associated protein (VAP) and bind to the cellular receptors; or by using agents which mimic the cellular receptor and bind to the VAP. This includes anti-VAP antibodies, receptor anti-idiotypic antibodies, extraneous receptor and synthetic receptor mimics (viral mimetics). Two such "entryblockers" or "viral mimetics" are amantadine and rimantadine. In certain aspects amantadine, rimantadine, or compounds with similar mechanisms of action can be used in composition described herein. In a further aspect amantadine and rimantadine can be formulated as a treatment for influenza.

A second approach to anti-viral therapy is to target the processes that synthesize virus components after a virus invades a cell. One way of doing this is to develop nucleotide or nucleoside analogues that look like the building blocks of RNA or DNA, but deactivate the enzymes that synthesize the RNA or DNA once the analog is incorporated. Nucleotide analogs include, but are not limited to ribivirin, vidarabine, acyclovir, gangcyclovir, zidovudine, didanosine, zalcitabine, stavudine, and lamivudine. A number of antiproliferative compounds are known to inhibit both cancers and viruses, thus other anti-proliferative compounds can be used as an anti-viral therapy.

Another approach is to inhibit sialidases (also referred to as neuraminidases). Sialidases hydrolyse alpha-(2/3)-, alpha-(2/6)-, alpha-(2/8)-glycosidic linkages of terminal sialic residues in oligosaccharides, glycoproteins, glycolipids, colominic acid, and synthetic substrates. Sialidases act as pathogenic factors in virus infections. Thus, sialidase inhibitors can be used to attenuate the ability of a virus to infect a subject.

Some viruses have a protease that cuts viral protein chains apart so they can be assembled into their final configuration. HIV includes a protease, and so considerable research has been performed to find "protease inhibitors" to attack HIV at that phase of its life cycle. Protease inhibitors became available in the 1990s and have proven effective.

The final stage in the life cycle of a virus is the release of mature viruses from the host cell. Two drugs (neuraminidase inhibitors, also referred to as sialidase inhibitors) named zanamivir (RELENZA™) and oseltamivir (TAMIFLU™) that have been introduced to treat influenza prevent the release of viral particles by blocking a molecule named neuraminidase that is found on the surface of flu viruses, and also seems to be constant across a wide range of flu strains.

Anti-viral drugs include, but are not limited to abacavir; acemannan; acyclovir; acyclovir sodium; adefovir; alovudine; alvircept sudotox; amantadine hydrochloride; amprenavir; aranotin; arildone; atevirdine mesylate; avridine; cidofovir; cipamfylline; cytarabine hydrochloride; delavirdine mesylate; desciclovir; didanosine; disoxaril; edoxudine; efavirenz; enviradene; envlroxlme; famciclovir; famotine hydrochloride; fiacitabine; fialuridine; fosarilate; trisodium phosphonoformate; fosfonet sodium; ganciclovir; ganciclovir sodium; idoxuridine; indinavir; kethoxal; lamivudine; lobucavir; memotine hydrochloride; methisazone; nelfinavir; nevlrapme; penciclovir; pirodavir; ribavirin; rimantadine hydrochloride; ritonavir; saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zidovudine; zinviroxime, interferon, cyclovir, alpha-interferon, and/or beta globulin.

In certain embodiments the antiviral drug is ribivirin or high dose ribivirin. Ribavirin is an anti-viral drug that is active against a number of DNA and RNA viruses. It is a member of the nucleoside antimetabolite drugs that interfere with duplication of viral genetic material. Though not effective against all viruses, ribavirin has wide range of activity, including important activities against influenzas, flaviviruses, and agents of many viral hemorrhagic fevers.

Typically, the oral form of ribavirin is used in the treatment of hepatitis C, in combination with pegylated interferon drugs. The aerosol form has been used in the past to treat respiratory syncytial virus-related diseases in children. However, its efficacy has been called into question by multiple studies, and most institutions no longer use it.

D. Other Agents

In certain aspects of the invention an anti-inflammatory agent may be used in combination with a composition described herein.

Steroidal anti-inflammatories for use herein include, but are not limited to fluticasone, beclomethasone, any pharmaceutically acceptable derivative thereof, and any combination thereof. As used herein, a pharmaceutically acceptable derivative includes any salt, ester, enol ether, enol ester, acid, base, solvate or hydrate thereof. Such derivatives may be prepared by those of skill in the art using known methods for such derivatization.

Fluticasone—Fluticasone propionate is a synthetic corticosteroid. Fluticasone propionate is a white to off-white powder and is practically insoluble in water, freely soluble in dimethyl sulfoxide and dimethylformamide, and slightly soluble in methanol and 95% ethanol. In an embodiment, the formulations of the present invention may comprise a steroidal anti-inflammatory (e.g., fluticasone propionate).

Beclomethasone—In certain aspects the steroidal antiinflammatory can be beclomethasone dipropionate or its monohydrate. The compound may be a white powder and is very slightly soluble in water (Physicians' Desk Reference), very soluble in chloroform, and freely soluble in acetone and in alcohol.

Providing steroidal anti-inflammatories according to the present invention may enhance the compositions and methods of the invention by, for example, attenuating any unwanted inflammation. Examples of other steroidal anti-inflammatories for use herein include, but are not limited to, betamethasone, triamcinolone, dexamethasone, prednisone, mometasone, flunisolide and budesonide.

In accordance with yet another aspect of the invention, the non-steroidal anti-inflammatory agent may include aspirin, sodium salicylate, acetaminophen, phenacetin, ibuprofen, ketoprofen, indomethacin, flurbiprofen, diclofenac, naproxen, piroxicam, tebufelone, etodolac, nabumetone, tenidap, alcofenac, antipyrine, amimopyrine, dipyrone, ammopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, meclofenamic acid, mefenamic acid, niflumic acid, salidifamides, sulindac, suprofen, tolmetin, nabumetone, tiaramide, proquazone, bufexamac, flumizole, tinoridine, timegadine, dapsone, diflunisal, benorylate, fosfosal, fenclofenac, etodolac, fentiazac, tilomisole, carprofen, fenbufen, oxaprozin, tiaprofenic acid, pirprofen, feprazone, piroxicam, sudoxicam, isoxicam, celecoxib, Vioxx®, and/or tenoxicam.

IV. Kits

Any of the compositions described herein may be comprised in a kit. In a nonlimiting example, reagents for production and/or delivery of a therapeutic composition described herein are included in a kit. In certain aspects the kit is portable and may be carried on a person much like an asthma inhaler is carried. The kit may further include a pathogen detector. The kit may also contain a gas or mechanical propellant for compositions of the invention.

The components of the kits may be packaged either in an aqueous, powdered, or lyophilized form. The container means of the kits will generally include at least one inhaler, canister, vial, test tube, flask, bottle, syringe or other container means, into which a component(s) may be placed, and preferably, suitably aliquoted. Where there is more than one component in the kit (second agent, etc.), the kit also will generally contain a second, third or other additional container into which the additional components may be separately placed. However, various combinations of components may be comprised in a vial, canister, or inhaler. A container of the invention can include a canister or inhaler that can be worn on a belt or easily carried in a pocket, backpack or other storage container. The kits of the present invention also will typically include a container for the described compositions or their variations, and any other reagent containers in close confinement for commercial sale. Such containers may include injection or blow molded plastic containers into which the desired vials are retained.

When the components of the kit are provided in one and/or more liquid solutions, e.g., the liquid solution is an aqueous solution, with a sterile aqueous solution being particularly preferred, but not required. However, the components of the kit may be provided as dried powder(s). When reagents and/or components are provided as a dry powder, the powder may be reconstituted by the addition of a suitable solvent or administered in a powdered form. It is envisioned that a solvent may also be provided in another container.

A kit will also include instructions for employing the kit components as well the use of any other reagent not included in the kit. Instructions may include variations that can be implemented.

It is contemplated that such reagents are embodiments of kits of the invention. Such kits, however, are not limited to the particular items identified above and may include any reagent used directly or indirectly in the detection of pathogenic microorganisms or administration of a composition described herein.

The inventors have used the mouse as model for microbial infection of the lung. Not be held to any particular mechanism or theory, it is believed that the increase in resistance to infection is due to activation of local defenses or innate immunity. The effects of single and repetitive exposure of a subject to a composition of the invention have been determined and no obvious gross pathology, such as premature death, weight loss, or behavioral changes have been observed.

One non-limiting benefit of the present invention is that it can be delivered and have effect quickly and easily. Also, the compositions can be produced economically in large quantities and easily stored, as well as easily transported by a person outside of a hospital setting. Typically, the administration of the inventive compositions and the methods of the invention result in at least some killing or inhibition of the invading pathogens even before cellular entry. In the case that some pathogens do enter cells in the lungs either by escaping extracellular killing or because the compositions are administered after pathogen exposure (preemptively) instead of before pathogen exposure (preventatively), it is contemplated that the compositions and related methods promote intracellular killing resulting from the enhanced or augmented local responses in the lungs.

A composition described in this application would simplify countermeasure stockpiling and deployment. Also, the compositions and methods of the invention would eliminate the difficulty of rapidly identifying a specific pathogen during a bioweapon attack or other exposure or potential exposure event. In addition, the economic advantages of producing and purchasing an agent with applicability in multiple civilian and biodefense settings are significant. Augmenting local epithelial mechanisms is particularly attractive in subjects who often have neutropenia or impaired adaptive immune function, e.g., immune compromised subjects. The methods typically act locally rather than systemically, and provide broad effects against multiple pathogens. The effects are rapid and are attractive in a biodefense, medical, and epidemic setting.

Augmentation of innate defense capabilities of the lungs in normal hosts would be valuable during influenza or emergent respiratory viral epidemics for which adaptive immune vaccines are not available. Similarly, protection of caregivers during an epidemic would facilitate care of the sick while limiting spread.

Many people in the community live with chronically compromised defenses against infection, such as patients with diabetes and patients taking immunosuppressive drugs for autoimmune diseases or to prevent transplant rejection. These people will benefit from a treatment or an increased resistance to infection during epidemics or times where potential for exposure to viruses is elevated. Even more strikingly, cancer patients undergoing chemotherapy who have transient but severely compromised immune defenses might benefit from transient protection. Pneumonia is a common occurrence in these patients, and is the leading cause of infectious death.

Resistance to infection can be stimulated to provide transient protection during prolonged periods of neutropenia. Other cancer patients, such as those receiving fludarabine or anti-lymphocyte antibodies, or those receiving calcineurin inhibitors and steroids after hematopoietic stem cell transplantation, have impaired adaptive immunity. These patients might also benefit from episodic stimulation of immunity to protect against epidemic viruses. Community outbreaks of seasonal respiratory viruses such as influenza, parainfluenza, and RSV can cause fatal pneumonia in these compromised patients, and infection with many of these viruses can be rapidly identified from nasal washings.

V. Viruses

Class A bioterrorism agents that can be transmitted by aerosol include smallpox virus, and hemorrhagic fever viruses. Class B and class C bioterrorism agents also can be effectively delivered by the respiratory route. These organisms comprise a variety of viral classes. Because of the potential difficulty in initially identifying a specific agent, the complexity of locally stockpiling adaptive immune vaccines and antibiotics directed at specific agents, and the remarkable virulence of organisms despite appropriate treatment, stimulation of innate defense capabilities and increasing the resistance of the lungs to infection can prevent or preempt or attenuate infection with an agent delivered by the respiratory route. Such an effect could have great public health value.

There are numerous microbes that are considered pathogenic or potentially pathogenic under certain conditions (i.e., opportunistic pathogens/microbes). In certain aspects, the pathogenicity is determined relative to infection via the lungs. In certain aspects the microbe is a virus. There are numerous viruses and viral strains that are considered pathogenic or potentially pathogenic under certain conditions.

Viruses can be placed in one of the seven following groups: Group I: double-stranded DNA viruses, Group II: single-stranded DNA viruses, Group III: double-stranded RNA viruses, Group IV: positive-sense single-stranded RNA viruses, Group V: negative-sense single-stranded RNA viruses, Group VI: reverse transcribing Diploid single-stranded RNA viruses, Group VII: reverse transcribing Circular double-stranded DNA viruses. Viruses include the family Adenoviridae, Arenaviridae, Caliciviridae, Coronaviridae, Filoviridae, Flaviviridae, Hepadnaviridae, Herpesviridae (Alphahelpesvirinae, Betaherpesvirinae, Gammaherpesvirinae), Nidovirales, Papillomaviridae, Paramyxoviridae (Paramyxovirinae, Pneumovirinae), Parvoviridae (Parvovirinae, Picornaviridae), Poxviridae (Chordopoxvirinae), Reoviridae, Retroviridae (Orthoretrovirinae), and/or Togaviridae. These viruses include, but are not limited to various strains of influenza, such as avian flu (e.g., H5N1). Particular virus from which a subject may be protected include, but is not limited to Cytomegalovirus, Respiratory syncytial virus and the like.

Examples of pathogenic viruses include, but are not limited to Influenza A, H5N1, Marburg, Ebola, Dengue, Severe acute respiratory syndrome coronavirus, Yellow fever virus, Human respiratory syncytial virus, Vaccinia virus and the like.

VI. Formulations and Administration

The pharmaceutical compositions disclosed herein may be administered via the respiratory system of a subject. In certain aspects the compositions are deposited in the lung by methods and devices known in the art. Therapeutic compositions described herein may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations contain a preservative to prevent the growth of microorganisms. The pharmaceutical forms suitable for inhalation include sterile aqueous solutions or dispersions and sterile powders for the extemporaneous preparation of sterile inhalable solutions or dispersions. In all cases the form is typically sterile and capable of inhalation directly or through some intermediary process or device. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like.

Some variation in dosage will necessarily occur depending on the condition of the subject being treated and the particular circumstances involving exposure or potential exposure. The person responsible for administration will, in any event, determine the appropriate dose for the individual subject. Moreover, for human administration, preparations should meet sterility, pyrogenicity, general safety, and purity standards as required by FDA Office of Biologics standards or other similar organizations.

Sterile compositions are prepared by incorporating the active components in the required amount in the appropriate solvent with various other ingredients enumerated above, as required, followed by, for example, filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile compositions, some methods of preparation are vacuum-drying and freeze-drying techniques which yield a powder of the component(s) and/or active ingredient(s) plus any additional desired ingredient from a previously sterile-filtered solution.

Pulmonary/respiratory drug delivery can be implemented by different approaches, including liquid nebulizers, aerosol-based metered dose inhalers (MDI's), sprayers, dry powder dispersion devices and the like. Such methods and compositions are well known to those of skill in the art, as indicated by U.S. Pat. Nos. 6,797,258, 6,794,357, 6,737,045, and 6,488,953, all of which are incorporated by reference. According to the invention, at least one pharmaceutical composition can be delivered by any of a variety of inhalation or nasal devices known in the art for administration of a therapeutic agent by inhalation. Other devices suitable for directing pulmonary or nasal administration are also known in the art. Typically, for pulmonary administration, at least one pharmaceutical composition is delivered in a particle size effective for reaching the lower airways of the lung or sinuses. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), Aerotech II® or the like.

All such inhalation devices can be used for the administration of a pharmaceutical composition in an aerosol. Such aerosols may comprise either solutions (both aqueous and non-aqueous) or solid particles. Metered dose inhalers typically use a propellant gas and require actuation during inspiration. See, e.g., WO 98/35888 and WO 94/16970. Dry powder inhalers use breath-actuation of a mixed powder. See U.S. Pat. Nos. 5,458,135 and 4,668,218; PCT publications WO 97/25086, WO 94/08552 and WO 94/06498; and European application EP 0237507, each of which is incorporated herein by reference in their entirety. Nebulizers produce aerosols from solutions, while metered dose inhalers, dry powder inhalers, and the like generate small particle aerosols. Suitable formulations for administration include, but are not limited to nasal spray or nasal drops, and may include aqueous or oily solutions of a composition described herein.

A spray comprising a pharmaceutical composition described herein can be produced by forcing a suspension or solution of a composition through a nozzle under pressure. The nozzle size and configuration, the applied pressure, and the liquid feed rate can be chosen to achieve the desired output and particle size. An electrospray can be produced, for example, by an electric field in connection with a capillary or nozzle feed.

A pharmaceutical composition described herein can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer.

In an ultrasonic nebulizer, high-frequency electrical energy is used to create vibrational, mechanical energy, typically employing a piezoelectric transducer. This energy is transmitted to the composition creating an aerosol.

In a metered dose inhaler (MDI) or in other device that us propellant, a composition, and any excipients or other additives are contained in a canister as a mixture with a compressed gas. Actuation of the metering valve releases the mixture as an aerosol. Pharmaceutical compositions for use with a metered-dose inhaler device will generally include a finely divided powder containing a composition of the invention as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a subject. The preparation of an aqueous composition that contains a polypeptide or peptide as an active ingredient is well understood in the art.

VII. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 5:
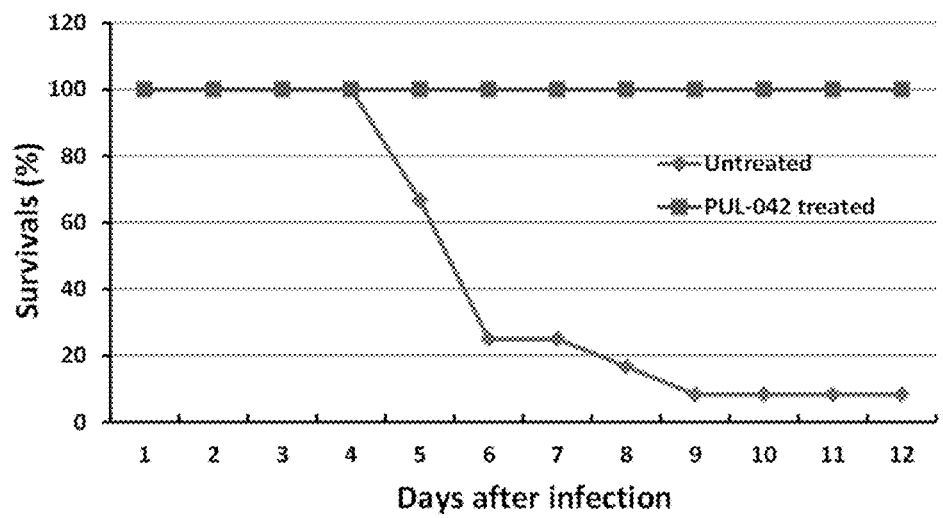
FIG. 5. Prior aerosolized PUL-042 treatment fully protects mice against lethal SARS-COV infection (−24 hrs; challenge dose: 5× $LD_{50}$).
Figure 6:
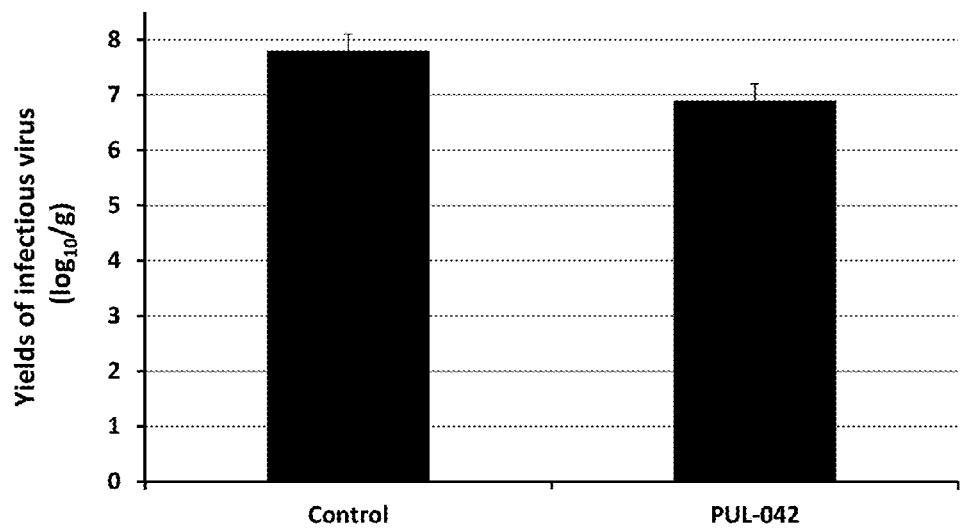
FIG. 6. Prior aerosolized PUL-042 treatment reduces pulmonary yields of infectious SARS-COV (−24 hrs; challenge dose: 5× LD50; 3 dpi).
Figure 7:
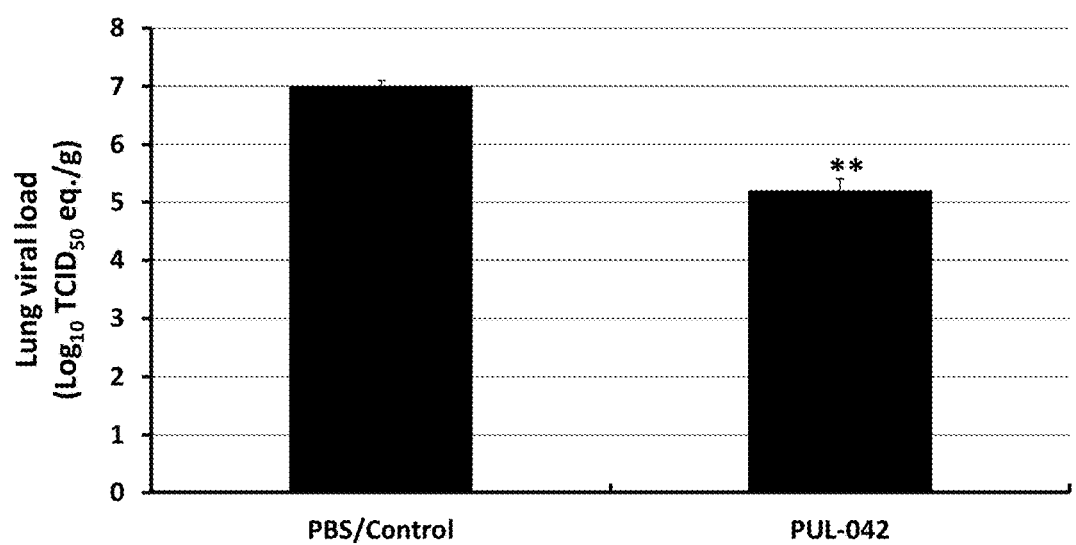
FIG. 7. Prior treatment with aerosolized PUL-042 significantly reduced the viral loads in MERS-COV-challenged mice (3 dpi).

Effect of Time and Frequency of PUL042 and Combination Treatments Against Influenza Studies were designed and performed to compare the effect of timing and frequency of aerosolized PUL042 (Pam2CSK4+ODN-M362) and oral or aerosolized Tamiflu (Oseltamivir phosphate) as combination treatments to inhibit pulmonary influenza A/HK/8/68 (H3N2) virus (FluA) infection in mice. Survival and body weights were followed up to 21 days. Similar studies were also conducted using the antiviral ribavirin (RBV). (See FIG. 1, FIG. 2, FIG. 3, and FIG. 4). Similar studies have been conducted with coronavirus such as MERS-COV and SARS-COV (See FIG. 5, FIG. 6, and FIG. 7).

Mice:

NIH Swiss-Webster, female, 6-8 weeks of age, approximately 20 g. On day 0 hour 0 mice are divided into groups and infected. Treats start at +48 h (day 2). Groups included the following:

Group 1: Untreated, infected control, no treatments.
Group 2: Water by gavage at +48, +72 and +96 h (no infection)
Group 3: Tamiflu by gavage at 4 mg/kg/day given at +48, +72 and +96 h
Group 4: Aerosol PUL042 at +48 h.
Group 5: Aerosol PUL042 at +48 and +96 h.
Group 6: Aerosol PUL042 plus Tamiflu by gavage at +48 h followed by Tamiflu by gavage at +72 and +96 h.
Group 7: Aerosol PUL042 plus Tamiflu by gavage at +48 and +96 h with Tamiflu by gavage at +72 h.
Group 8: Aerosol PUL042/Tamiflu combination at +48 h.
Group 9: Aerosol PUL042/Tamiflu combination at +48 and +96 h with aerosol Tamiflu at +72 h.
Group 10: aerosol Tamiflu at +48, +72 and +96 h

PUL-042:

16 µM Pam2CSK4+4 µM ODN-M362 formulated and supplied by Pulmotect for each aerosol exposure. Five (5) mL for 15 min aerosol treatments are needed (total for 3 exposures=20 mL of PUL042).

Virus:

Influenza A/HK/8/68 (H3N2; Mouse Lung Pool Jan. 17, 2012). Stock titer=7.64 $\log_{10}$ $TCID_{50}$/mL. Dilute virus 1:500 in 0.05% gelatin-MEM [1:500=20.0 µL to 10 mL of 0.05% gelatin-MEM]; use 9 mL in reservoir of nebulizer. Titer is determined in pre- and post-nebulization reservoir solutions. Estimated virus/mouse when exposed to aerosol for 20 min with Aerotech II nebulizer flowing at 10 L/min air ~$10^5$ $TCID_{50}$.

Virus Infection:

Half of the mice from each group is randomized into 1 of 2 treatment boxes and exposed to influenza virus aerosol for 20 min. Virus and drug exposures are generated from an Aerotech II nebulizer flowing at 10 L/min of room air generated from an Aridyne 2000 compressor.

PUL042 Treatments:

Mice are placed into a sealed plastic box. For PUL042 treatment, a selected group of mice is administered aerosol of PUL042 for 15 min. After exposure, mice are returned to their pre-assigned groups.

Oral Tamiflu (Oseltamivir Phosphate) Gavage Treatments:

Oseltamivir phosphate is obtained from Tamiflu capsules. For gavage, powder from 1 capsule (163 mg/capsule; 45% oseltamivir carboxylate equivalent) is suspended in 1 mL of sterile water, vortexed, and sonicated in a water bath at room temperature for 1-5 min. The solution is equivalent to 75 mg oseltamivir carboxlyate/mL. For each treatment, Tamiflu is diluted and administered by gavage (oral) using 100 µL of 0.8 mg Oseltamivir carboxylate/mL (dilute: 0.424 mL of 75 mg Osel/mL+39.576 mL $H_2O$) for a dose of 4 mg/kg/day in 100 pt.

Aerosols of PUL042 and/or Tamiflu:

Oseltamivir phosphate is obtained from Tamiflu capsules. For each day's aerosol, powder from 5 or 6 capsules (167±1 mg/capsule; 45.0% oseltamivir carboxylate equivalent) is suspended in 5 or 6 mL of either PUL042 (combination) or in sterile water (Tamiflu-only) and vortexed vigorously. The suspension is centrifuged at full speed in the clinical centrifuge for 15 min and the supernatant fraction is removed and place in the nebulizer. The solution is equivalent to 75 mg oseltamivir carboxlyate/mL. The estimated deposition is 1.7 mg/kg in the lungs and 3.4 mg/kg in the stomach.

Procedures:

On Day 0, all Groups are exposed to a 20 min aerosol calculated to deposit approximately $10^5$ $TCID_{50}$ of FluA/HK per mouse (approximately 85-100% mortality). Mice are returned to their appropriate groups and weighed.

On Day +2 (+48 h), Group 1 is treated with oral water; Groups 4, 5, 6, and 7 are treated with aerosolized PUL042; Groups 3, 6, and 7 are treated with Oral Tamiflu; Groups 8 and 9 are treated with a combination of PUL042 and Tamiflu; Group 10 is treated with aerosolized Tamiflu.

On Day +3 (+72 h), Group 1 is treated with oral water; Groups 3, 6, and 7 are treated with oral Tamiflu; and Groups 9 and 10 are treated with aerosolized Tamiflu.

On Day +4 (+96 h), Group 1 is treated with oral water; Groups 5 and 7 are treated with aerosolized PUL042; Groups 3, 6, and 7 are treated with Oral Tamiflu; Group 9 is treated with combination PUL042 and Tamiflu; and Group 10 is treated with aerosolized Tamiflu.

Mice in each group are observed daily for overt illness, morbidity, and mortality. Mice are weighed on Days 0, 4 through 11; and days 14 to 21, if necessary.

Protocol:

| Group[1] | Aerosol Dose: | Duration Aerosol (min) | Oral Dose (mg/kg/day) q.d. | Drug Treatment (day) | FluA Challenge Day 0 | Endpoints |
|---|---|---|---|---|---|---|
| 1 | 0 | None | 0 | None | Yes | Body weights; Survival |
| 2 | 214 + 266 ng/kg/day[2] | 15 | — | +2, 3, 4 | No | |
| 3 | | 15 | 4 | +2, 3, 4 | Yes | |
| 4 | | 15 | — | +2 | Yes | |
| 5 | | 15 | — | +2, 4 | Yes | |
| 6 | | 15 | 4 | +2, 3, 4 | Yes | |
| 7 | | 15 | 4 | +2, 3, 4 | Yes | |
| 8 | 214 + 266 ng/kg/day[2]; | 15 | — | +2 | Yes | |
| 9 | | 15 | — | +2, 3, 4 | Yes | |
| 10 | L: 1.7 S: 3.4 mg/kg/d[3] | 15 | — | +2, 3, 4 | Yes | |

[1]Mice, 15/group;
[2]Estimated deposited dosage of Pam2CSK4 + ODN-M362, 16 µM Pam2 + 4 µM ODN;
[3]Estimated deposited dosage (mg/kg/day) of aerosolized Oseltamivir (75 mg/mL) in lungs (L) and stomach (S).
Abbreviations: Rx = treatment; Combo, combination PUL042 aerosol + oral or aerosolized Tamiflu; FluA = influenza A/HK/8/68 (H3N2) virus.

Timing of Treatments:

| Group | Day 0 | Day 1 | Day 2 | Day 3 | Day 4 | Total Rx (days) |
|---|---|---|---|---|---|---|
| 1 | Virus | — | — | — | — | None |
| 2 | Virus | — | Water-g | Water-g | Water-g | 3 |
| 3 | Virus | — | O-g | O-g | O-g | 3 |
| 4 | Virus | — | P | — | — | 1 |
| 5 | Virus | — | P | | P | 2 |
| 6 | Virus | — | P + O-g | O-g | O-g | 3 |
| 7 | Virus | — | P + O-g | O-g | P + O-g | 3 |
| 8 | Virus | — | P + O-aer | — | — | 1 |
| 9 | Virus | — | P + O-aer | O-aer | P + O-aer | 3 |
| 10 | Virus | — | O-aer | O-aer | O-aer | 3 |

P + O-g or P + O-aer = Combo Rx, PUL042 aerosol + Oral or aerosolized Tamiflu; O-g = Tamiflu Oral only; O-aer, Tamiflu Aerosol only.
Abbreviations:
H, water;
O, Oseltamivir as Tamiflu;
P, PUL042;
g, gavage;
a, aerosol;
D, day of treatment Example 2

Dose-Response and Temporal Efficacy of Aerosolized PUL-042 Administered in Combination with Ribavirin in Attenuating RSV Infection RSV is a major cause of pneumonia and bronchiolitis in infants, the elderly, and immunocompromised transplant patients, and is a major cause of respiratory infection leading to asthma exacerbations. Further, an immune-suppressed model has been described in which cotton rats (CR) treated with cyclophosphamide exhibit characteristics of persistent RSV infection. These conditions are physiologically relevant to studies targeting immune-suppressed populations at risk for RSV infections. In addition, more than 200 CR genes have been cloned encoding cytokines, chemokines, and lymphocyte cell surface markers. Analysis of these genes can inform mechanisms of viral pathogenesis and clearance in the presence or absence of therapeutic treatments.

Using aerosolized forms of both drugs given alone or in combination, the comparative effects of a single dose versus two doses, and of treatment begun early after infection, or relatively late in the course of infection is evaluated.

The studies use an established animal model for RSV infection, the cotton rat, to evaluate the ability of addition of PUL-042 to ribavirin treatment to inhibit viral infection and replication in the nasopharyngeal compartment and compare this to the activity in the lung, which is more representative of later stage or more severe viral disease.

Cotton rats are the optimal model for these studies because they are 100-fold more permissive than mice to RSV infections in both the upper and lower airways, and infected animals develop pathology similar to that seen in humans. The predictive quality of the CR model for therapeutics in treating RSV infections advanced clinical trials of RSVIg, Respigam and palivizumab, and an effective protocol for Ribavirin treatment is well established in the cotton rat.

Experimental Methods

RSV Inoculation and PUL-042 Drug Delivery

*Sigmoden hispidis* cotton rats (CR) are ~75-150 g body weight as determined by the age at start of the experiment. Animal body weight and sex distribution is as similar as possible across all groups at the start. Body weights are recorded at end of the experiment. RSV/A/Tracy, $1.22 \times 10^5$ PFU is given to CR lightly anesthesized with isoflurane. For PUL-042 or ribavirin treatment, CR are placed into a sealed plastic box. PUL-042 and ribavirin exposures are generated from a Pari LC Sprint nebulizer flowing at 10 L/min of room air generated from a compressor.

Lung and Nasal Tissue Homogenates and Histopathology:

Following $CO_2$ euthanasia, for the same animal, one lung lobe is clamped off for organ homogenate and the remaining lobes are perfused with 10% neutral buffered formalin, and inflated for paraffin embedding. To evaluate the upper airways, one nasal turbinate is prepared for histopathology and the other is used to prepare tissue homogenates. Plaque assays are performed on the lung and nasal homogenates. Total RNA is extracted from lung and nasopharyngeal tissues and the kinetics of RSV genome replication is measured by RT-qPCR. This total lung RNA may also be used to evaluate expression of cotton rat genes associated with pathogenesis of RSV disease.

Histopathology:

Intact lung tissue from the formalin-fixed lobes is prepared for histology. Sections are stained with hematoxylin-eosin and coded for blinded scoring of histopathology by veterinary pathologists. Sections are scored from 0 to 4 based on the extent and severity of alveolitis, alveolar eosinophilia, bronchiolitis, bronchiolar eosinophilia, peribronchiolar mononuclear inflammatory cell infiltrates, and perivascular mononuclear inflammatory cell infiltrates.

In these experiments, PUL-042 and ribavirin are at the concentrations (nebulized in 5 mL water as ribavirin at 100 mg/mL; PUL-042 at 17 µg/mL ODN+11.6 µg/mL PAM2) applied in prior mouse influenza A experiments. All experiments are repeated once for confirmation of results.

Evaluate the Optimal Start of Treatment and Interval of Treatment.

In prior experience with PUL-042 combined with ribavirin against influenza A, it was found that two sequential combination treatments on days 1 and 2 post-infection resulted in a 92% increased survival rate, whereas ribavirin alone on those two days provided only minimal improvement in survival rate, at 15%, compared to 0% of untreated. The greatest efficacy of PUL-042 as a monotherapy was found when the drug was administered on Day 1 post-infection (approximately 40% survival) with the benefit dropping rapidly if treatment was further delayed.

Dose Schedules of PUL-042=/−Ribavirin in RSV-infected cotton rats.

| Group | RSV | PUL-042 | RBV | Combination | Viral Titer Evaluation |
|---|---|---|---|---|---|
| Control 1 | Infected | UT | UT | UT | D 4 |
| Control 2 | Infected | UT | UT | UT | D 5 |
| Control 3 | Infected | D −1 | UT | UT | D 4 |
| Control 4 | Infected | D 1 + D 2 | UT | UT | D 4 |
| Control 5 | Infected | UT | D 1 + D 2 | UT | D 4 |
| Treatment 1 | Infected | UT | UT | D 1 + D 2 | D 4 |
| Treatment 2 | Infected | UT | UT | D 1 + D 3 | D 4 |
| Treatment 3 | Infected | UT | UT | D 1 + D 4 | D 5 |
| Treatment 4 | Infected | UT | UT | D 2 + D 3 | D 4 |
| Treatment 5 | Infected | UT | UT | D 2 + D 4 | D 5 |

UT = Untreated;
D −1 = 24 h before infection;
D 1 = Day 1 post-infection

The RSV infection in CR is not lethal. Demonstration of an effect of PUL-042 and ribavirin for RSV requires measurement of viral load during the course of infection and clearance, and evaluation of histopathology during the course of RSV disease in the same animals. The effect of two doses of PUL-042 and ribavirin initiated on day 1 post-infection, followed by a second treatment on Day 2, or Day 3, or Day 4 and those initiated on day 2 post-infection, followed by treatment on Day 3 or Day 4 is evaluated. For treatment schedules ending before Day 4, animals are euthanized for analysis on Day 4. In addition to untreated controls for evaluation on days 4 and 5, ribavirin is evaluated alone administered on Day 1 and Day 2 with evaluation of Day 4 titers. Because the day of maximal proliferation is Day 4, and RSV is cleared in these animals by Day 7, any treatment occurring after Day 4 may not be distinguishable from the result in untreated animals.

Simulation of Treatment in an Immune-Suppressed Patient Population.

The optimal time course and dosing schedule can be repeated in cotton rats undergoing cyclophosphamide (CY) treatment and the effect of PUL-042 alone or combined with ribavirin is measured. As previously described, intraperitoneal dosing of CY maintains a state of leukopenia in cotton rats without affecting mortality. RSV infection in CY-treated CR is persistent as shown by prolonged high titers in lung tissue at 12 days post-infection. CR are given CY intraperitoneal (i.p.) injections of 50 mg/kg three times per week for 3 weeks before RSV infection, and continues until the end of the time course for each animal. Immunosuppression is confirmed by complete blood counts (CBC) in blood collected at necropsy by cardiac puncture from CY-treated and untreated control animals. In addition to the day 4 time point for measuring virus titers, titers are measured in the CY-immune suppressed animals at day 10 to confirm persistent RSV infection and to determine what effect PUL-042 has on virus replication later in infection. Serum cytokines levels are also measured in the blood samples.

The invention claimed is:

1. A composition comprising: a co-formulation of (a) PAM2CSK4, (b) type C CpG oligodeoxynucleotide TLR 9 agonist, and (c) antiviral pharmaceutical selected from oseltamivir and ribavirin, wherein the composition is formulated for administration to the lungs by nebulization or aerosolization.

2. The composition of claim 1, wherein the type C CpG oligodeoxynucleotide is ODN2395 or ODNM362 or ODN10101.

3. A method of treating, inhibiting, or attenuating a viral infection comprising administering an effective amount of the composition of claim 1 to an individual that has or is at risk of viral infection.

4. The method of claim 3, wherein the subject has been exposed to a virus.

5. The method of claim 3, wherein the virus is a Adenoviridae, Coronaviridae, Filoviridae, Flaviviridae, Hepadnaviridae, Herpesviridae, Orthomyxoviridae, Paramyxovirinae, Pneumovirinae, Picomaviridae, Poxyiridae, Retroviridae, or Togaviridae.

6. The method of claim 3, wherein the virus is Parainfluenza, Influenza, H5N1, Marburg, Ebola, Severe acute respiratory syndrome coronavirus (SARS-COV), Middle eastern respiratory syndrome coronavirus (MERS-COV), yellow fever virus, human respiratory syncytial, Hantavirus, or Vaccinia virus.

7. The method of claim 3, wherein the composition is administered by nebulization.

8. The method of claim 3, wherein the lipopeptide, immune stimulatory oligonucleotide and anti-viral drug are administered in an amount of from about 0.1 mg/kg to about 100 mg/kg of the individual's body weight.

9. A method of treating, inhibiting, or attenuating a viral infection comprising administering an effective amount of a composition comprising in an aerosolized formulation: (a) PAM2CSK4, (b) type C CpG oligodeoxynucleotide TLR9 agonist, and (c) antiviral pharmaceutical selected from oseltamivir and ribavirin, to an individual that has or is at risk of viral infection.

10. The method of claim 9, wherein the type C oligodeoxynucleotide TLR9 agonist is ODN2395 or ODNM362 or ODN 10101.

11. A nebulizer comprising (a) PAM2CSK4, (b) type C CpG oligodeoxynucleotide TLR9 agonist, and (c) anti-viral pharmaceutical selected from oseltamivir and ribavirin.

* * * * *

UNITED STATES PATENT AND TRADEMARK OFFICE
CERTIFICATE OF CORRECTION

PATENT NO. : 10,286,065 B2
APPLICATION NO. : 14/860205
DATED : May 14, 2019
INVENTOR(S) : Burton Dickey et al.

Page 1 of 1

It is certified that error appears in the above-identified patent and that said Letters Patent is hereby corrected as shown below:

In the Claims

In Claim 10, at Column 26, Line 58, please delete "ODN 10101" and add --ODN10101--.

Signed and Sealed this
First Day of September, 2020

Andrei Iancu
*Director of the United States Patent and Trademark Office*